(12) United States Patent
San Gabriel et al.

(10) Patent No.: US 7,271,257 B2
(45) Date of Patent: Sep. 18, 2007

(54) GLUTAMATE RECEPTORS AND UTILIZATION THEREOF

(75) Inventors: Ana San Gabriel, Kawasaki (JP);
Hisayuki Uneyama, Kawasaki (JP);
Takami Maekawa, Kawasaki (JP);
Kunio Torii, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/922,166

(22) Filed: Aug. 20, 2004

(65) Prior Publication Data
US 2006/0040350 A1 Feb. 23, 2006

(51) Int. Cl.
*C12N 15/12* (2006.01)
(52) U.S. Cl. .................. 536/23.5; 435/69.1; 435/252.3; 435/320.1
(58) Field of Classification Search ...................... None
See application file for complete search history.

(56) References Cited

U.S. PATENT DOCUMENTS 5,385,831 A * 1/1995 Mulvihill et al. .......... 435/69.1

OTHER PUBLICATIONS

Masu et al. Sequence and Expression of a Metabotropic Glutamate Receptor. Feb. 28, 1991, Nature 349:760-765.*
Berk, M. et al., "Platelet Glutamate Receptor Supersenitivity in Major Depressive Disorder", *Clinical Neuropharmacology*, vol. 24, No. 3, pp. 129-132, (2001).
Karim, F. et al., "Metabotropic Glutamate Receptor Subtypes 1 and 5 Are Activators of Extracellular Signal-Regulated Kinase Signaling Required for Inflammatory Pain in Mice", *The Journal of Neuroscience*, vol. 21, No. 11, pp. 3771-3779, (2001).
Berk, M. et al., "The Specificity of Platelet Glutamate Receptor Supersensitivity in Psychotic Disorders", *Life Sciences*, vol. 66, No. 25, pp. 2427-2432, (2000).
Carlton, S. M. et al., "Inflammation-induced changes in peripheral glutamate receptor populations", *Brian Research*, vol. 820, pp. 63-70, (1999).
Haxhiu, M. A. et al., "The role of excitatory amino acids in airway reflec responses in anesthetized dogs", *Journal of the Autonomic Nervous System*, vol. 67, pp. 192-199, (1997).
Inagaki, N. et al.,. "Expression and role of ionotropic glutamate receptors in pancreatic islet cells", *The FASEB Journal*, vol. 9, pp. 686-691, (1995).
Erdö, S. L., "Exitatory amino acid receptors in the mammalian periphery", *TRENDS in Pharmacological Sciences*, vol. 12, pp. 426-429, (1991).
Aas, P. et al., "Stimulation of peripheral cholinergic nerves by glutamate indicates a new peripheral glutamate receptor", *European Journal of Pharmacology*, vol. 164, pp. 93-102, (1989).

Said, S. I. et al., "Glutamate signalling in the lung", *TRENDS in Pharmacological Sciences*, vol. 22, No. 7, pp. 344-345, (2001).
Skerry, T. M. et al., "Glutamate signalling in non-neuronal tissues", *TRENDS in Pharmacological Sciences*, vol. 22, No. 4, pp. 174-181, (2001).
Bray, G. A., "Afferent signals regulating food intake", *Proceeding of the Nutrition Society*, vol. 59, pp. 373-384, (2000).
Bray, G. A., "Nutrient Balance and Obesity: An Approach to Control of Food Intake in Humans", *Medical Clinics of North America*, vol. 73, No. 1, pp. 29-45, (1989).
Mei, N., "Recent studies on intestinal vagal afferent innervation. Functional implications", *Journal of the Autonomic Nervous System*, vol. 9, pp. 199-206, (1983).
Mei, N. et al., "Current data and ideas on digestive sensitivity", *Journal of the Autonomic Nervous System*, vol. 41, pp. 15-18, (1992).
Mei, N., "Intestinal Chemosensitivity", *The American Physiological Society*, vol. 65, No. 2, pp. 211-237, (1985).
Pin, J. et al., "Alternative splicing generates metabotropic glutamate receptors inducing different patterns of calcium release in Xenopus oocytes", Proc. Natl. Acad. Sci. USA, vol. 89, pp. 10331-10335, (1992).
Kasahara, J. et al., "Insitol phospholipid metabolism in Xenopus oocytes mediated by endogenous $G_o$ and $G_i$ proteins", *Federation of European Biochemical Societies*, vol. 355, pp. 41-44, (1994).
Takahashi, K. et al., "Role of the Large Extracellular Domain of Metabotropic Glutamate Receptors in Agonist Selectivity Determination", *The Jounral of Biological Chemistry*, vol. 268, No. 26, pp. 19341-19345, (1993).
Naples, M. A. et al., "Pharamcological profiles of the metabotropic glutamate receptor ligands [$^3$H] L-AP4 and [$^3$H] CPPG", *Neuropharmacology*, vol. 40, pp. 170-177, (2001).
Thomsen, C. et al., "Cloning and Characterization of a Metabotropic Glutamate Receptor, mGluR4b", *Neuropharmacology*, vol. 36, No. 1, pp. 21-30, (1997).
Adams, S. R. et al., "Fluorescence ratio imaging of cyclic AMP in single cells", *Nature*, vol. 349, pp. 694-697, (1991).
McConnell, H. M. et al., "The Cytosensor Microphysiometer: Biological Applications of Silicon Technology", *Science*, vol. 257, pp. 1906-1912, (1992).
Hermans, E. et al., "Structural, signalling and regulatory properties of the group I metabotropic glutamate receptors: prototypic family C G-protein-coupled receptors", Biochem. J., vol. 359, pp. 465-484, (2001).
Niijima, A., "Effects of Oral and Intestinal Stimulation with Umami Substance on Gastric Vagus Activity", *Physiology & Behavior*, vol. 49, pp. 1025-1028, (1991).

* cited by examiner

*Primary Examiner*—John Ulm
(74) *Attorney, Agent, or Firm*—The Nath Law Group; Susanne M. Hopkins; Ari G. Zytcer

(57) ABSTRACT

An isolated DNA molecule which encodes a novel glutamate receptor and a transformed cell expressing the receptor are provided.

3 Claims, 10 Drawing Sheets mGluR1 protein homology across species

```
MGLUR1  370  ENYVQDSKMGFVINAIYAMAHGLQNMHHALCPGHVGLCDAMKPIDGRKLLDFLIK  424 rat
MGLUR1  402  ENYVQDSKMGFVINAIYAMAHGLQNMHHALCPGYVGLCDAMKPIDGRKLLDFLIK  456 mouse
MGLUR1  402  ENYVQDSKMGFVINAIYAMAHGLQNMHHALCPGHVGLCDAMKPIDGSKLLDFLIK  456 human
MGLUR4  398  SAYEQEGKVQFVIDAVYAMGHALHAMHRDLCPGRVGLCPRMDPVDGTQLLKYIRN  452 rat
T1R1    379  LGAFSMSAAYNVYEAVYAVAHGLHQLLGCTSGTCAR------GPVYPWQLLQQIYK  428 mouse MGLUR1  425  SSFVGVSGEEVWFDEKGDAPGRYDIMNLQY  454  rat
MGLUR1  457  SSFVGVSGEEVWFDEKGDAPGRYDIMNLQY  486  mouse
MGLUR1  457  SSFIGVSGEEVWFDEKGDAPGRYDIMNLQY  486  human
MGLUR4  453  VNFSGIAGNPVTFNENGDAPGRYDIYQYQL  482  rat
T1R1    429  VNFLLHKKT--VAFDDNGDPLGYYDIIAWDW  457  mouse
```

Figure 1A

5' transcript sequence homology between rat and mouse

RAT    TTTGTTTATAGATATCTCTGAACTCATTTGTGAGACACTGTCTTCTTCTTCTCTCTTCACCCCAACCCCTGCATTGTTTAGT
       ||||||||||||||||||||||||||||||||||||| |||||||  |    |   ||||||||||||||||||||||||||
MOUSE  TTTGTTTATAGATATCTCTGAACTCATTCA-TGAGACGTT----GTCTTCTTCTCTCTCTTCACCCCAACCCCTGCACTGTTTAGT

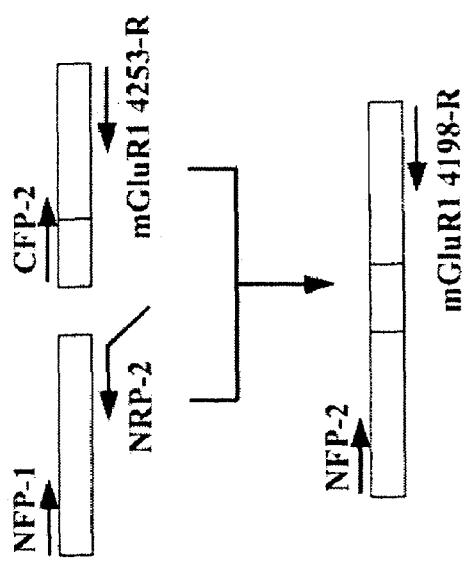
Fig 6a
Fig 6b
Figure 6

GLUTAMATE RECEPTORS AND UTILIZATION THEREOF

BACKGROUND OF THE INVENTIVE SUBJECT MATTER

1. Technical Field of the Inventive Subject Matter

The inventive subject matter relates to novel glutamate receptors and utilization thereof; more specifically to a glutamate receptor, DNA which encodes the receptor, a transformed cell expressing the receptor, a method for producing the receptor, a method for identifying an agonist, antagonist, or allosteric modulator for glutamic acid, a method for identifying an agonist for glutamic acid, an antibody to the receptor, and processes for making glutamate receptor modulators and pharmaceutical compositions comprising said modulator.

2. Background

Glutamic acid is a major excitatory neurotransmitter in the central nervous system, and it is widely accepted that its abnormal control is involved in progressive encephalopathies such as memory disorders, ischemic encephalopathy, amyotropic lateral sclerosis (ALS), Parkinson's disease, and Huntingon's chorea (Meldrum, B. S., Neurology, 1994 November;44 (11 Supple 8):S14-23; Nishizawa, Y., Life Sci. 2001, Jun. 15;69(4):369-81). Therefore, many studies concerning glutamate receptors have been carried out up to now in cranial nerve system. Many receptors (three kinds of ionotropic receptors and eight kinds of metabotropic receptors) have been found in the central nervous system with their splicing variants as well. Particularly, since 1992 when metabotropic glutamate receptor type I (mGluR1a) was cloned by Nakanishi, et al., at least three splicing variants (mGluR1b, mGluR1c and mGluR1d) have been confirmed as mGluR1 variants (As to details, refer to Hermans, E. and Challiss, R. A., Biochemical J., 359:465-484, 2001). In all of those variants, the C-terminal region of mGluRla becomes short, and their existence in nerve cells and glia cells has been confirmed. On the basis of such abundant receptor information, development for working drugs which are specific to each receptor has been extensively carried out. Even today new therapeutic drugs in the treatment of the above-described diseases are being developed (As to details, refer to Barnard, E. A., Trends Pharmacol. Sci., 1997, May;18(5):141-8; Schoepp, D. D., Conn. P. J., Trends Pharmacol. Sci., 1993, January; 14(1):13-10).

Nowadays, we have several pieces of knowledge that suggest physiological functions of the peripheral glutamate receptor (Berk, M., Plein, H., Ferreira, D., Clin. Neuropharmacol., 2001, May-June;24(129-32; Karim, F., J. Neurosci. 2001, Jun. 1;21(11):3771-9; Berk, M., Plein, H., Belsham, B., Life Sci. 2000;66(25):2427-32; Carlton, S. M., Goggeshall, R. E., Brain Res. 1999, Feb. 27; 820(1-2):63-70; Haxhij. M. A., Erokwu, B., Dreshaj, I. A., J. Auton. Nerv. Syst. 1997, Dec. 11; 67(3):192-9; Inagaki, N., FASEB J. 1995, May; 9(8):686-91; Erdo, S. L., Trends Pharamcol. Sci., 1991, November; 12(11):426-9; Aas, P., Tanso, R., Formum, F., Eur. J. Pharamacol. 1989, May 2; 164(1):93-102; Said, S. I., Dey, R. D., Dickman, K., Trends Pharmacol. Sci. 2001, July; 22(7):344-5; Skerry, T. M., Genever, P. G., Trends Pharmacol., Sci. 2001, April; 22(4):174-81). However, those peripheral glutamate receptors are expressed in peripheral nerves, smooth muscle and immune tissues. There has been no report for their expression in epithelium of tongue and digestive tract. In mammals including humans to maintain normal growth and health, it is necessary to orally take up required amounts of nutrients at a specific timing and excrete disposable matter. This is actually done by the digestive tract, which is a single tube consisting of oral cavity, stomach, small intestine and large intestine. The process of digestion and absorption is controlled by intrinsic intestinal neuroplexus and extrinsic cranial nerves.

The judgment as to whether or not to take a necessary nutrient is the result of brain integration of a signaling pathway that the individual is aware of taste with an autonomous signaling pathway that the individual is unaware of visceral sense. It is considered that salty taste (sodium, potassium, etc.) serves as a marker of minerals and is required for maintaining the osmotic pressure of the body fluid; sweetness (glucose) serves as a marker of carbohydrates and is required for supplementing energy; umami (sodium glutamate) serves as protein marker and is useful for supplementing energy and essential amino acids; and bitterness serves as a marker for toxic substances. That is, necessary nutrients are taken up relying on the tastes thereof. Then, if necessary amounts are ingested, satiation is determined by a series of intracerebral processes coming from the signal input to the solitary tract nucleus. Those signals are derived from activated vagus afferent fibers through nutrient sensors existing in the stomach, small intestine, and hepatoportal vein (Bray, G. A., Proc. Nutr. Soc., 2000; 59:373-84; Bray G. A., Med. Clin. North. Am. 1989:73:29).

On the other hand, physiological studies on the mechanism for chemical sensation in the digestive tract have been performed for a long time. It is supposed that there are sensors that detect the content of the digestive tract (for the details, reference is made to Mei, N., J. Auton. Nerv. Syst., 1983; 9:199-206; Mei, N., Lucchini, S., J. Auton, Nerv. Syst., 1992; 41:15-8). The digestive chemosensory system includes a glucose sensor (Mei, N., J. Physiol. (Lond.) 1978, 282, 485-5-6), a temperature sensor (El Ouazzani, T., Mei, N., Exp. Brain Res. 1979; 15; 34:419-34), an osmotic pressure sensor (Mei, N., Garnier, L., J. Auton. Nerv. Syst., 1986; 16:159-70), a pH sensor, an amino acid sensor (Mei, N., Physiol. Rev., 1985; 65:211-37), and a stretch sensor (Barber, W. D., Burks, T. F., Gastroenterol Clin. North. Am. 1987; 16:521-4).

In particular, a sensor that recognizes glutamic acid was suggested by Niijima et al. from neural excitation that occurred when glutamic acid was administered in the digestive tract. In this experiment, the technique of recording neural discharge activity was used for the stomach branch and abdominal cavity branch of the vagus nerve. Those vagal branches control mainly the stomach and small intestine and responded to glutamic acid; therefore was assumed that there is a mechanism that recognizes this amino acidat the vagus nerve ending (Niijima, A., Physiol. Behav., 1991; 49:1025-8). However, no cloning has been made for such a supposed sensor that recognizes glutamic acid until Applicants' present work.

DISCLOSURE OF THE INVENTION

Although many studies have been made on glutamate receptors and digestive tract sensors as described above, to date, glutamate perception is unclear and no progress has been made in recent works. Failure of receptor isolation from tissues containing glutamate sensors (receptor, transporter, etc.) necessary for nutrient recognition in the mucous membrane of the digestive tract prevented the progress in this research field. Applicants expect that elucidation of the umami-like substances that bind to glutamate sensors in the digestive tract would enable development of drugs and the like directed to control of the nutrient recognition mechanism described below.

That is, the nutrient recognition mechanism also plays an important role on satiety or surfeit and improves poor physical condition in edacity and imbalance when indulging nutrients in eating disorders. It is considered that abnormal recognition of nutrients in the digestive tract naturally results in disturbance in the overall process of digestion and absorption, thus causing edacity, eating disorders, inappetence, indigestion, diarrhea, constipation, etc. Medically, there are many factors involved in the development of digestive diseases such as ulcers (stomach ulcer, duodenum ulcer) due to psychogenetic hyperphagia, cibophobia, obesity, anomaly of acid secretion, anomaly of blood flow in digestive tract, anomaly of secretion of digestive enzymes, etc., stress ulcers, drug-caused (NSAIDs, etc.) acute ulcers, ischemic ulcer (ischemic colitis), diabetes due to anomaly of secretion of insulin or anomaly of secretion of digestive tract hormone, heavy stomach, nausea, constipation, diarrhea, hypersensitivity bowel syndrome, etc. due to anomaly of gastrointestinal motility and so forth.

Further, in recent years, the abrupt increase in obesity incidence is a social phenomenon. Many of those who are obese are said to have decreased basal metabolism and tend to eat too much. How to control the appetite of obese individuals is of great social concern. Many try to be on an excessive diet. However, in most cases, they are unsuccessful. Thus, improving the mechanism of nutrient recognition in the digestive tract and achieving satiety with a normal meal is very important to those who are obese.

The second object of the inventive subject matter is derived from the above-described viewpoint, and the matter to be solved is identification of an actual glutamate-like substance which binds to glutamate sensors in the epithelium of the digestive tract andmethods forutilizing such sensors are provided.

Applicants have investigated a receptor distribution in the epithelium of the tongue and in the digestive tract by way of an immunohistological methods using antibodies that recognize the intracellular domain of the metabotropic glutamate receptor type 1 (mGluR1). As a result, it has been found that cells in the epithelium of the tongue and the mucous membrane layer of the stomach are positive for mGluR1 where the receptor is present. In the tongue epithelium, the apical site of taste cells from taste buds are positive for mGluR1. Whereas in the stomach, mucus-secreting cells (neck mucus cells) and pepsinogen-secreting cells (chief cells) at the body of the stomach and mucous cells at the antrum of the stomach are positive for mGluR1. cDNA cloning from tongue epithelium was first performed, which has produced novel glutamate receptors, including that having the nucleic acid sequence of SEQ ID NO: 19 and is gustatory bud type mGluR1β, type A (hereinafter referred to "taste mGluR1" or "taste mGluR1 variant"). The taste mGluR1 is found in the taste buds and in the mucosal cells in the stomach. It is expected that this glutamate receptor is a novel umami taste receptor. Furthermore, Applicants are assiduously investigating whether the stomach contains another mGluR1 variant in the mucosal cells. It is expected that this would be a digestive tract glutamate sensor, which was previously unknown, and that the receptor cDNA, a purified receptor, and the receptor-expressing cells are useful for screening for modulators of digestive tract glutamate sensor.

The inventive subject matter has been achieved on the basis of the above findings and its summary is as follows.

(1) An isolated protein of glutamate receptor of following (A) or (B):
  (A) a protein which comprises the amino acid sequence of SEQ ID NO: 2;
  (B) a protein which comprises the amino acid sequence of SEQ ID NO: 2 with at least one substitution from:
    (a) His 26 to Tyr,
    (b) Arg 39 to Ser, and
    (c) Val 51 to Ile.
(2) The glutamate receptor protein according to (1), wherein said protein is expressed in mucosal cells of rat stomach.
(3) An isolated DNA of following (a), (b), or (c):
  (a) DNA encoding glutamate receptor protein having amino acid sequence of SEQ ID NO: 2,
  (b) DNA which comprises nucleic acid sequence of SEQ ID NO: 1 or 442-2169 of SEQ ID NO: 1,
  (c) DNA which hybridizes with a DNA molecule having the nucleotide sequence of SEQ ID NO: 1 under stringent conditions and followed with two washes at 60° C. in a solution comprising a salt concentration of 0.1×SSC and 0.1% SDS.
(4) A cell which holds DNA coding for the glutamate receptor protein described in (3) in an expressible form.
(5) A method for the search of agonist, antagonist or allosteric modulator for glutamic acid, characterized in that, the glutamate receptor protein described in any of (1) to (2) is made to react with a substance which bonds to that protein in the presence of a substance to be tested whereupon inhibition or promotion of the reaction is detected.
(6) A method for the search of agonist for glutamic acid, characterized in that, the glutamate receptor protein described in any of (1) to (2) is made to react with a substance to be tested whereupon the reaction is detected.
(7) The method according to (6), wherein the glutamate receptor protein from the cell of (4) or a membrane fraction prepared from the cell is used.
(8) The method according to (5), wherein inhibition or promotion of the above bond is detected by a second messenger generated by the glutamate receptor protein.
(9) The method according to (7), wherein the glutamate receptor protein from the cell of (4) or a membrane fraction prepared from the cell is used.
(10) An antibody which specifically bonds to the glutamate receptor protein described in any of (1) to (2).
(11) A method for the manufacture of a drug for the adjustment of a second messenger which is generated by bonding of glutamic acid to a glutamate receptor comprising:
  a step where the glutamate receptor protein described in any of (1) to (2) is made to react with a substance which bonds to said protein in the presence of a substance to be tested to detect inhibition or promotion of the reaction whereby agonist, antagonist or allosteric modulator for glutamic acid is searched; and
  a step where a pharmaceutical composition is prepared using the agonist, antagonist or allosteric modulator for glutamic acid prepared in the above step as an effective ingredient.
(12) A method for the manufacture of a drug for the adjustment of a second messenger which is generated by bonding of glutamic acid to a glutamate receptor comprising:
  a step where the glutamate receptor protein described in any of (1) to (2) is made to react with a substance to be tested to detect inhibition or promotion of the reaction whereby agonist for glutamic acid is searched; and a step where a pharmaceutical composition is prepared using the agonist for glutamic acid prepared in the above step as an effective ingredient.

The inventive subject matter will now be illustrated in detail as hereunder.

Typically, an inventive glutamate receptor protein is a protein having an amino acid sequence represented by amino acid nos. 1 to 576 in SEQ ID NO: 2 in the Sequence Listing. An open reading domain of a base sequence of rat cDNA coding for an inventive protein is shown in SEQ ID NO: 1.

Since a variant of the glutamate receptor protein as such is a metabotropic glutamate type 1 receptor (mGluR1) of a stomach type found from mucosal cells, Applicants named it as stomach mGluR1. In mGluR1, there have been two known types, i.e. type A (mGluR1a) and type B (mGluR1b), depending upon the splicing variation of the C-terminal. An inventive protein encoded by SEQ ID NO: 1 is a variation of type A (mGluR1a). Hereinafter, the glutamate receptor proteins of the inventive subject matter may be generally referred to as mGluR1 variant in the present specification. When an appropriate promoter is linked to the upstream region of the base sequence represented by SEQ ID NO: 1 and is expressed within an appropriate cell line, Applicants have produced active glutamate receptors.

Comparison of the amino acid sequence of the inventive subject matter with that of brain-type metabotropic glutamate type 1 receptor (hereinafter referred to as mGluR1, accession number: M61099, SEQ ID NO: 14), an inventive receptor has a truncated N-terminus. The first methionine for the stomach mGluR1 corresponds to the residue M410 in the brain-type metabotropic glutamate receptor. The mGluR1 variant isolated from taste tissue also contains this truncation at the amino end of the receptor. The rest of the amino acid sequence for all currently known variants, including brain-type, taste-type, and stomach-type mGluR1, is identical until the sequence encoding the intracellular domain. At the C-terminus, the stomach-type mGluR1 is spliced at the K952 residue (numbering corresponds to the receptor sequence for the brain-type receptor). After the corresponding lysine 952, an inventive protein contains a novel peptide sequence of 33 amino acids shown in SEQ ID NO: 18. This amino acid sequence is not present in the brain-type mGluR1. The sequence detail is shown in FIGS. 2 and 3.

Thus, the mGluR1 variants of the inventive subject matter have the same transmembrane domain as type 1 metabotropic glutamate receptor protein, but demonstrate differences in the intracellular domain and the extracellular domain when compared with the type 1 receptor. The extracellular domain of the inventive mGluR1 is the active site for glutamic acid but binding affinity is different from brain mGluR1. Other brain mGluR1 agonists such as quisqualic acid, ibotenic acid, ACPD (1-aminocyclopentane-trans-1,3-dicarboxylic acid) and so on may function as ligands with inventive mGluR1.

Despite the fact that the intracellular domain of the mGluR1 variant of the inventive subject matter is different from that of mGluR1, the binding site for G proteins at the C-terminus is conserved. A shorter C-terminus seems to affect the electrophysiological response induced by receptor activation (Mary et al., J Biol. Chem. 1998 Jan. 2; 273 (1):425-32); nevertheless, the mGluR1 variant is still considered to be a functional receptor which is able to generate a second messenger.

The stomach mGluR1 of the inventive subject matter may be derived from a rat. Alternatively, so long as it can generate a second messenger when glutamic acid is bound thereto, the mGluR1 variant may be derived from any animal, including mammals such as human, monkey, mouse, dog, cow, rabbit, birds, and fish.

In the case where the mGluR1 variant is used as a component of pharmaceutical composition, it is preferably derived from a mammal. The truncation site at the N-terminus has an amino acid sequence highly conserved among the rat, mouse, and human. The nucleotide sequence at the intron site where the N-terminus splicing site occurs in the rat is very similar to the mouse, as shown in FIG. 1. The intron structure that yields the N-terminal truncation in the rat stomach and gustatory (taste) mGluR1 variants seems to be also present in the mouse. Therefore, those conserved sequences are an indication that a corresponding variant is expected to exist in mouse and human.

The mGluR1 variant of the inventive subject matter may be a protein having the amino acid sequence of SEQ ID NO: 2, including substitution, deletion, insertion or addition of one or a plurality of amino acids at one or a plurality of sites, so long as the mGluR1 variant has the property of generating a second messenger when glutamic acid is bound thereto. In particular, such substitutions, deletions, insertions or additions may occur in the same manner that species-differences occur among rat, mouse, human, monkey, dog, cow, and rabbit. Since an exemplary sequence of the inventive subject matter derives from rat, the candidate amino acid for such substitution is easily found by sequence comparison using commercially available homology comparison software. An exemplary partial comparison is shown in FIG. 1. Particularly, preferable substitutions are His in 26th position for Tyr, Arg in 39th position for Ser, and Val in 51th position for Ile (position numbers corresponds to those in SEQ ID NO: 2). The inventive subject matter includes all such variations as long as the variant-specific, truncated sites are conserved.

The term "plurality" as used herein varies depending on the positions of amino acid residues in the three-dimensional structure of the protein and the types of the amino acids. However, the number may be such that the homology with the amino acid sequence shown by SEQ ID NO: 2 is 80% or more, preferably 90% or more. More particularly, a plurality is 2 to 115 amino acids, preferably 2 to 58 amino acids, more preferably 2 to 30 amino acids.

An inventive glutamate receptor may be in a purified or isolated form; however, when the activity is required, it is preferably in a form that is expressed in a suitable cell and localized in the membrane of the cell or in a form contained in a membrane fraction prepared from a cell in which the mGluR1 variant was expressed. Thus, the inventive subject matter also includes cells that express an mGluR1 variant, or a membrane fraction prepared from such cells.

An inventive mGluR1 variant can be obtained, for example, by introducing DNA that encodes the mGluR1 variant into a suitable host cell to express the mGluR1 variant. The above-described DNA includes DNA that encodes the mGluR1 variant, isolated from the chromosome of a cell of a mammal such as mouse. When chromosomal DNA is used, it is preferable that cDNA is used since it is considered necessary to control a post-transcriptional process such as splicing so that mGluR1 variant can be generated.

The cDNA of an mGluR1 variant can be cloned by amplifying the cDNA of mGluR1 variant using RNA prepared from the epithelium of the tongue of a mammal such as a rat as a template, and oligonucleotides shown in the embodiments as primers. In addition, since the structure of an mGluR1 variant, particularly the unique structure in the N-terminal region, has been determined as described herein, the cloning and identification of the cDNA of mGluR1 variant can be performedeasily based on the disclosed structures. Theopen reading frame nucleotide sequence of the cDNA of mGluR1 variant thus obtained is shown in SEQ ID NO: 1.

Thus, another feature of the inventive subject matter is a polynucleotide coding for an inventive mGluR1 variant. With regard to the polynucleotide coding for an inventive mGluR1 variant, any polynucleotide which contains a nucleic acid base sequence, whether DNA or RNA, preferably DNA, coding for an above-described mGluR1 variant of the inventive subject matter may be used, provided that the polynucleotide does not code for brain-type mGluR1. Such a polynucleotide is DNA or RNA, such as mRNA, coding for the mGluR1 variant of the inventive subject matter and may be double-stranded or single-stranded. In the case of a double-stranded polynucleotide, it may be double-stranded DNA, double-stranded RNA or a DNA:RNA hybrid. In the case of a single-stranded polynucleotide, it may be a sense or coding strand, or an anti-sense or non-coding strand. Typically, the polynucleotide is a polynucleotide having a base sequence represented by SEQ ID NO: 1.

The DNA which encodes the mGluR1 variant includes, in addition to the nucleotide sequence shown in SEQ ID NO: 1, DNA which hybridizes with DNA having this nucleotide sequence of SEQ ID NO: 1, or a probe that can be prepared from the same nucleotide sequence under stringent conditions and that encodes the mGluR1 variant. The term "stringent conditions" means conditions whereby a specific hybrid is formed, but nonspecific hybrids are not formed. It is difficult to clearly express the conditions by numeric values; examples thereof include those conditions whereby DNAs having high homology, for example, DNAs having 50% or more, preferably 75% or more homology hybridize with each other but DNAs having a lower homology than that will not hybridize with each other, or those conditions whereby DNAs hybridize with each other under ordinary washing conditions in southern hybridization, i.e., at 60° C. in a salt concentration corresponding to 1×SSC, 0.1% SDS, preferably 0.1×SSC, 0.1% SDS. Alternatively, when the probe having nucleic acid sequence of SEQ ID NO: 16 is used for the hybridization, stomach-specific hybrid is expected to be formed.

Cells into which DNA encoding the mGluR1 variant is introduced preferably include animal cells, insect cells or yeast when the activity of mGluR1 variant is required to be maintained, with animal cells being particularly preferable. Examples of cells that are expected to enable transient expression of mGluR1 activity by introducing a recombinant vector containing DNA encoding the mGluR1 variant include *Xenopus laevis* oocyte, Chinese hamster ovary (CHO) cell, baby hamster kidney (BHK) cell, human embryonic kidney (HEK) cell, Sf-9 insect cell, PC12 cell, and CACO-2 cell. In addition, when DNA encoding the mGluR1 variant is incorporated into chromosomal DNA to express the mGluR1 variant permanently, the cells described, other than the *Xenopus laevis* oocyte, are suitable.

With regard to a method for introduction of DNA coding for mGluR1 variant, publicly known methods may be used. Technique which is necessary for the operations such as an operation of introduction of DNA into cells is described in Sambrook, J., Fritsch, E. F. and Maniatis, T. "Molecular Cloning, A Laboratory Manual, Second Edition", Cold Spring Harbor Laboratory Press (1989), etc.

On the other hand, when no physiological activity is necessary such as the case where the mGluR1 variant is used as an immunogen for preparing antibody that specifically binds to the mGluR1 variant, cells to which DNA encoding the mGluR1 variant is introduced may be those cells that do not express the mGluR1 variant in an active form. As such cells, microbial cells that are usually used for the production of heterologous protein, including *Escherichia coli* may be used.

To produce the mGluR1 variant in the host cell, DNA, which encodes the mGluR1 variant, is ligated to an expression regulation sequence such as promoter or enhancer suitable for the host cell. The DNA which encodes the mGluR1 variant may include a processing information site, for example, a ribosome binding site, an RNA splicing site, a polyadenylation site, and a transcription terminator sequence as necessary. Preferable expression control sequences include promoters derived from immunoglobulin gene, SV40, adenovirus, bovine papilloma virus, and cytomegalovirus.

The techniques necessary for the manipulation of cells such as introduction of DNA therein are described in, for example, Sambrook, J., Fritsch, E. F., and Maniatis, T., "Molecular Cloning A Laboratory Manual, Second Edition", Cold Spring Harbor Laboratory Press, (1989).

The mGluR1 variant and a cell that retains the mGluR1 variant can be produced by cultivating a cell that harbors the DNA encoding the mGluR1 variant obtained as described above in an expressible form in a medium to produce the mGluR1 variant.

Active mGluR1 variant, that is, mGluR1 variant that can generate a second messenger when glutamic acid is bound thereto can be utilized for screening agonist, antagonist or allosteric modulator of glutamic acid. For example, the mGluR1 variant and a substance that binds to the mGluR1 variant are reacted in the presence of a test substance, and inhibition or promotion of the reaction is detected, thereby screening agonist, antagonist or allosteric modulator of glutamic acid (hereinafter, these may be referred to collectively as "ligand"). The allosteric modulator binds to a site other than the binding site between the mGluR1 variant and glutamic acid to exhibit similar function to that of the agonist or antagonist.

Further, the agonist of glutamic acid may be screened by reacting the mGluR1 variant with a test substance and detecting the reaction.

The active mGluR1 variant may include cells that express the mGluR1 variant or membrane fractions prepared from such cells. Such membrane fractions may be prepared by allowing cells to express active mGluR1 variant, ultrasonically disrupting the cells, and subjecting the sonicate to density gradient centrifugation to collect a membrane fraction.

Further, examples of the substance that binds to the above-described mGluR1 variant include glutamic acid, glutamic acid agonist, or known ligands that bind to mGluR1 (L-AP4, CPPG, MAP-4, or the like). The substances that modulate the activity of the mGluR1 variant include drugs that influence the intracellular concentration of calcium (calcium channel and sodium channel opener, Na/K pump inhibitor, Na/Ca exchange agonist, Ca-ATPase inhibitor, protein kinase C agonist), drugs that influence intracellular cAMP concentration (phosphodiesterase agonist, adenylate cyclase agonist), and drugs that influence intracellular cGMP concentration (cGMP-dependent phosphodiesterase agonist, guanylate cyclase agonist) and so forth.

Inhibition or promotion of the reaction between mGluR1 variant and a substance that binds thereto can be detected by measuring a second messenger that is generated by binding of a ligand such as glutamic acid to the mGluR1 variant. Alternatively, the above-described inhibition or promotion of reaction can also be detected by measuring the binding of a labeled known ligand to the mGluR1 variant instead of detecting the second messenger.

Further, the reaction between the mGluR1 variant and the agonist of glutamic acid can be detected by measuring a second messenger that is generated by binding of the mGluR1 variant to the agonist of glutamic acid.

The intracellular domain of stomach mGluR1 variant lacks 267 amino acid (about 800 bp) from that of the brain type mGluR1, type A. Despite such difference, brain, gustatory bud and stomach type mGluR1 have the same basic intracellular signal transmitting mechanism. The above-described second messenger is a rise in intracellular calcium concentration accompanied by the production of inositol triphosphate (IP3) as a result of activation of Gq (GTP binding protein) followed by activation of phospholipase C. In the downstream area of calcium variation in signal transduction, there are functional adjustments of the critical stage by phosphorylation of cytoplasmic and membrane proteins, and by gene expression adjustment via intracellular calcium-dependent protein kinase. Therefore, it is possible to detect second messengers other than IP3 and calcium by measurement of intracellular cAMP, cGMP changes and channel function change as a result of activation of calcium-dependent phosphodiesterase, protein phosphorylation of cell membrane fraction, etc.

Hereinafter, specific methods for searching a ligand using mGluR1 variant will be exemplified.

(1) mGluR1 variant cRNA is expressed in oocytes of *Xenopus* and a ligand acting on mGluR1 variant is searched by a two-electrode voltage cramp method using increase or decrease in intracellular calcium-depending chloride current (Pin, J. P., et al., Proc. Natl. Acad. Sci. USA, 1992 Nov. 1; 89(21):10331-5; Kasahara, J., Sugiyama, H., FEBS Lett., 1994 Nov. 21; 355(1):41-4; Takahashi, K., et al., J. Biol. Chem., 1993 Sep. 15; 268)26):19341-5).

(2) A candidate compound for ligand and known ligand acting on mGluR1 (such as glutamic acid, quisqualic acid, ibotenic acid, ACPD (1-aminocyclopentane-trans-1,3-dicarboxylic acid), CHPG ((RS)-2-chloro-5-hydroxy-phenylglycine), MPEP (2-methyl-6-(phenylethynyl)-pyridine), LY367385, etc.) are acted on a mGluR1 variant-expressing cell or a membrane fraction prepared from that cell for a certain period and amount of the known ligand bound to cell membrane of the mGluR1 variant-expressing cell or the membrane fraction is measured to conduct a ligand search (Naples, M. A., Neuropharmacology, 2001; 40(2):170-7; Thomsen, C., Neuropharmacology, 1997 January; 36(1):21-30; H. I. Yamamura, S. J. Enna and M. J. Kuhar, eds. 1958, Neurotransmitter Receptor Binding, 2nd ed., Raven Press, New York). Amount of the known ligand is able to be measured by the amount of radioactivity bound to the cell membrane or the membrane fraction after a radioactive labeling of a part of such substances.

(3) A calcium-sensitive dye (for example, Fura-2, Indo-1, Fluo-3 or the like) is introduced into an mGluR1 variant expressing cell in advance, and a ligand candidate compound and the mGluR1 variant expressing cells are allowed to contact for a certain period of time, and then ligands are screened by using as an index a change in a ratio of intensities of fluorescence (intracellular calcium concentration). Alternatively, screening of ligand is performed by a change in a ratio of intensities of fluorescence (intercellular calcium concentration) obtained when an mGluR1 variant agonist, a candidate compound for ligand, and an mGluR1 variant expressing cells into which a calcium-sensitive dye is introduced are allowed to contact for a certain period of time.

(4) Screening of ligands is performed by using as an index a change in a ratio of intensities of fluorescence (intracellular cAMP concentration) obtained when a cAMP-sensitive fluoroprotein (for example, FICRhR or the like) is introduced into an mGluR1 variant expressing cell in advance and then a ligand candidate compound and the mGluR1 variant expressing cells are allowed to contact for a certain period of time (Adams S R, Nature 1991 Feb. 21; 349(6311): 694-7).

(5) Screening of ligands is performed by using as an index the production amount of proton obtained when a candidate compound for ligand and an mGluR1 variant expressing cells are allowed to contact for a certain period of time, or when an mGluR1 variant agonist, a candidate compound for ligand and an mGluR1 variant expressing cells are allowed to contact for a certain period of time and measured by a cytosensor (McConnell H M, Science 1992 Sep. 25; 257 (5078):1906-12).

A food additive containing agonist, antagonist or allosteric modulator of glutamic acid searched as described above as an effective ingredient is able to be used as a novel umami taste-adjusting substance. Further, a pharmaceutical composition containing agonist, antagonist or allosteric modulator of glutamic acid searched as described above as an effective ingredient is able to be used as a drug for the adjustment of second messenger generated by binding of glutamic acid to a glutamate receptor. When the second messenger is adjusted, it is now possible that diseases and symptoms caused by abnormality of the glutamate receptor are improved and prevented.

The anomalies of control of vagus nerve include anomaly of afferent pathway (disorder of nutrient recognition) and anomaly of efferent pathway. The diseases or pathology due to the anomaly of afferent pathway include hyperphagia, cibophobia, obesity and so on. On the other hand, those due to the anomaly of efferent pathway include digestive ulcers (stomach ulcer, duodenal ulcer) due to psychogenetic hyperphagia, cibophobia, obesity, anomaly of acid secretion, anomaly of blood flow in digestive tract, anomaly of secretion of digestive enzymes, etc., stress ulcers, drug-caused (NSAIDs, etc.) acute ulcers, ischemic ulcer (ischemic colitis), diabetes due to anomaly of secretion of insulin or anomaly of secretion of digestive tract hormone, heavy stomach, nausea, constipation, diarrhea, hypersensitivity vowel syndrome, etc. due to anomaly of motility and so forth.

Use of mGluR1 variant as an immunogen enables preparation of an antibody that specifically binds to the mGluR1 variant. In particular, since the mGluR1 variant has a novel amino acid sequence in the C-terminus, antibody, particularly monoclonal antibody, that contains this portion as an epitope is expected to bind to the mGluR1 variant and not to bind to other glutamate receptors. The antibody specific to the mGluR1 variant can be used in immunostaining specific to the mGluR1 variant. Further, when the amino acid residue of the novel C-terminal intracellular domain is estimated from the three-dimensional structure forecast, it is possible to prepare an mGluR1 variant-specific antibody. An antibody which is specific to mGluR1 variant is able to be used for an immunostaining which is specific to mGluR1 variant, etc.

BRIEF DESCRIPTION OF THE DRAWINGS

FIG. 1A is a sequence alignment which shows mGluR1 protein homology across species: rat mGluR1 (SEQ ID NO: 25), mouse mGluR1 (SEQ ID NO: 26), human mGluR1 (SEQ ID NO: 27), rat mGluR4 (SEQ ID NO: 28). and mouse T1R1 (SEQ ID NO: 29).

FIG. 1B is a sequence alignment which shows 5' transcript sequence homology between rat (SEQ ID NO: 19, nucleotides 73-166) and mouse (SEQ ID NO: 25).

Figure 2A:
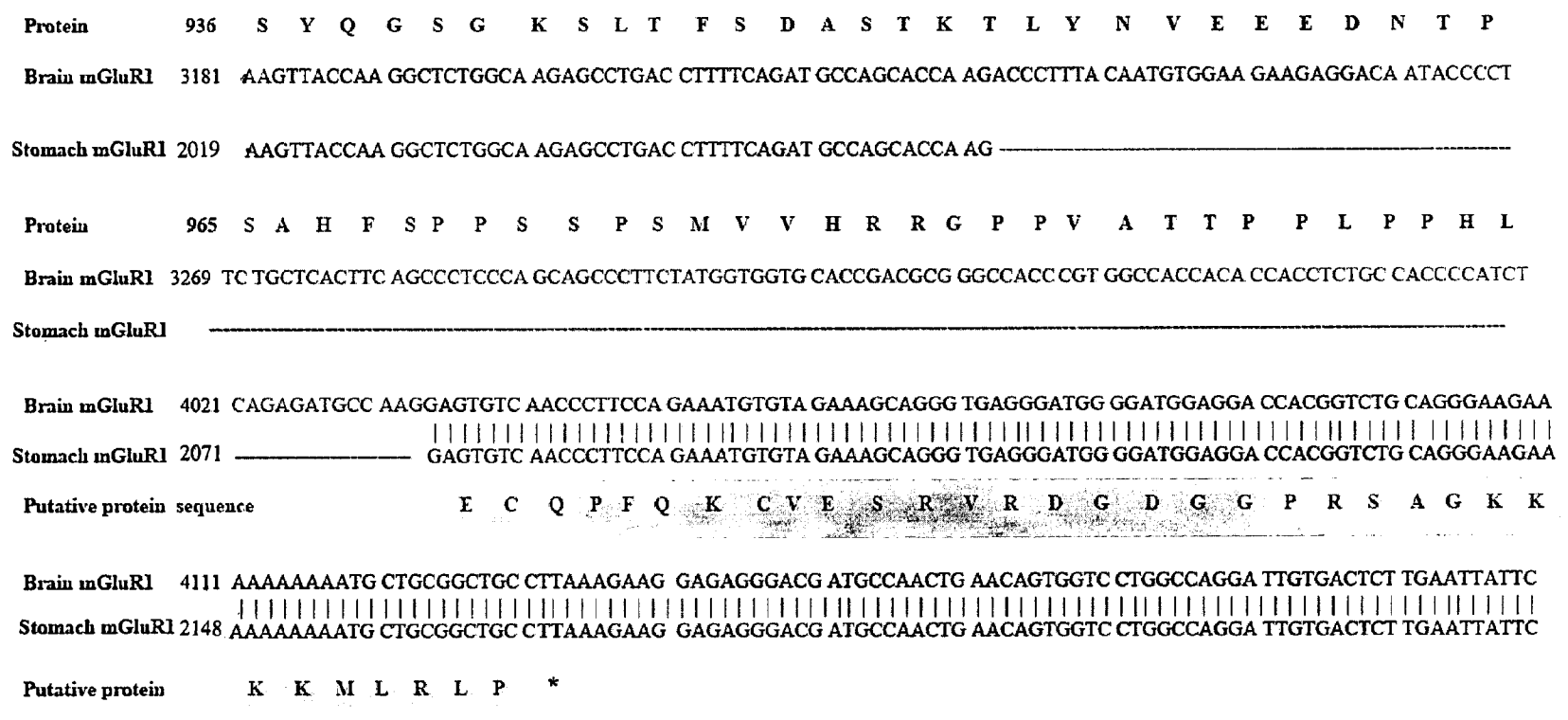

FIG. 2A is a sequence alignment which shows a sequence comparison of mGluR1 in C-terminus; the 3' mGluR1 sequence cloned from stomach (SEQ ID NO: 1, residues 2019-2237) is aligned with the corresponding mGluR1 a splicing variant Brain type mGluR1 (SEQ ID NO: 14, nucleotides 3181-4200, and amino acids 936-995), accession number M61099.

FIG. 6a is a drawing which shows crossover PCR and PCR primers used in the Examples herein. Primers were designed to specifically target the truncated region NPR-2 and CFP-2.

FIG. 6b is a photograph of an agarose gel which depicts the full sequence cDNA produced by linking the PCR products of the reaction shown in FIG. 6a in a final reaction generating a combined fragment.

DETAILED DESCRIPTION OF THE INVENTION

Figure 2B:
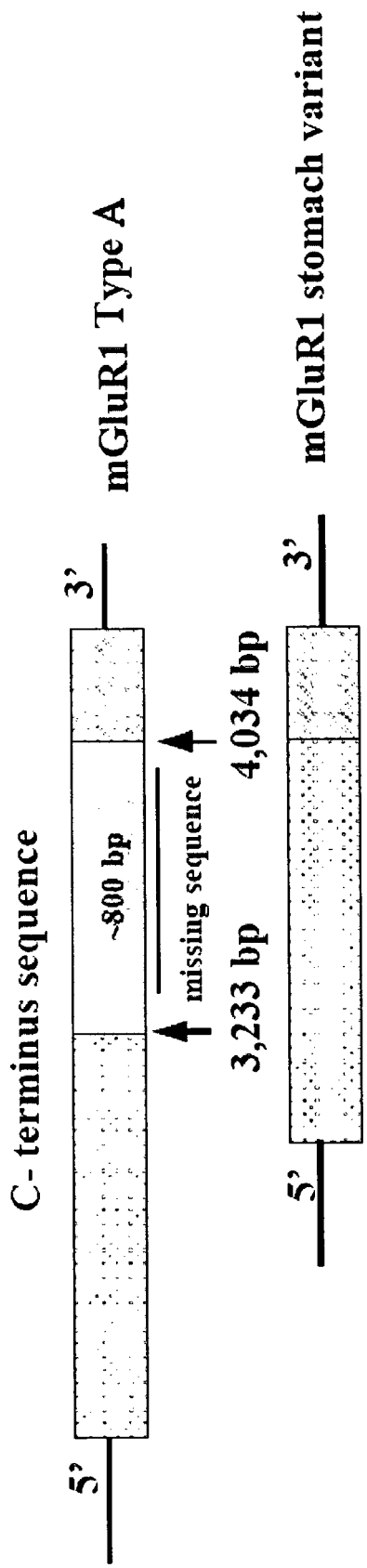
FIG. 2b is a sequence alignment which shows how a truncated C-terminus comes from the conjugation of proximal and distal ends between truncation as indicated in the diagram. There is around 800 bp missing.

The inventive subject matter relates to an isolated glutamate receptor protein, comprising:
(A) the amino acid sequence of SEQ ID NO: 2; or
(B) the amino acid sequence of SEQ ID NO: 2 with at least one amino acid substitution selected from the group consisting of:
  (a) His 26 to Tyr,
  (b) Arg 39 to Ser,
  (c) Val 51 to Ile, and
  (d) combinations thereof.

In another aspect of the inventive subject matter, said glutamate receptor protein is expressed by the mucosal cells in the stomach of rat.

The inventive subject matter further relates to an isolated DNA molecule, comprising:
  (a) a nucleic acid sequence encoding a glutamate receptor protein selected from the group consisting of:
    (A) the amino acid sequence of SEQ ID NO: 2, or
    (B) the amino acid sequence of SEQ ID NO: 2 with at least one amino acid substitution selected from the group consisting of:
      (i) His 26 to Tyr,
      (ii) Arg 39 to Ser,
      (iii) Val 51 to Ile, and
      (iv) combinations thereof;
  (b) a nucleic acid sequence of SEQ ID NO: 1;
  (c) a nucleic acid sequence of residues 442-2169 of SEQ ID NO: 1; or
  (d) a nucleic acid sequence which hybridizes with a DNA molecule having the nucleotide sequence of SEQ ID NO: 1 under stringent conditions and followed with two washes at 60° C. in a solution comprising a salt concentration of 0.1×SSC and 0.1% SDS.

The inventive subject matter additionally relates to a host cell transformed with an isolated DNA molecule coding for the glutamate receptor protein, as described above, in an expressible form.

In a preferred embodiment, said isolated DNA molecule in an expressible form comprises a vector. One of ordinary skill in the art will understand that there a many expression vectors known in the art and commercially available today.

In addition, the inventive subject matter relates to a method for identifying an agonist, antagonist, or allosteric modulator for glutamic acid, comprising the steps of:
  (a) in the presence of a substance to be tested, reacting a glutamate receptor protein according to claim 1 with a substance which binds to said glutamate receptor protein; and
  (b) detecting inhibition or promotion of said reaction.

In a preferred embodiment, said method for detecting inhibition or promotion of said binding is by detecting a second messenger generated by the glutamate receptor protein.

In another aspect, said glutamate receptor protein is prepared from a cell as described above, or a membrane fraction prepared from said cell.

The inventive subject matter also relates to a method for identifying an agonist for glutamic acid, comprising the steps of:
  (a) reacting a glutamate receptor protein according to claim 1 with a substance to be tested; and
  (b) detecting said reaction.

In a preferred embodiment, said method for detecting inhibition or promotion of said binding is by detecting a second messenger generated by the glutamate receptor protein.

In an alternate aspect, said glutamate receptor protein is prepared from a cell as described above, or a membrane fraction prepared from said cell.

The inventive subject matter further relates to an antibody which specifically binds to a glutamate receptor protein as described above.

Additionally, the inventive subject matter relates to an active agent for modulating a second messenger which is generated by binding of glutamic acid to a glutamate receptor, produced by a process comprising the steps of:
- (a) in the presence of a substance to be tested, reacting a glutamate receptor protein according to claim 1 with a substance which binds to said protein;
- (b) detecting inhibition orpromotion of said reaction; and
- (c) analyzing said inhibition or promotion of said reaction by said substance to be tested, and determining whether said substance to be tested is an agonist, antagonist, or allosteric modulator for glutamic acid.

The inventive subject matter additionally relates to a pharmaceutical composition comprising:
- (a) an active agent for modulating a second messenger which is generated by binding of glutamic acid to a glutamate receptor, produced by a process comprising the steps of:
  - (i) in the presence of a substance to be tested, reacting a glutamate receptor protein according to claim 1 with a substance which binds to said protein;
  - (ii) detecting inhibition or promotion of said reaction; and
  - (iii) analyzing said inhibition or promotion of said reaction by said substance to be tested, and determining whether said substance to be tested is an agonist, antagonist, or allosteric modulator for glutamic acid; and
- (b) a pharmaceutically acceptable carrier.

Further, the inventive subject matter relates to an active agent for modulating a second messenger which is generated by binding of glutamic acid to a glutamate receptor, produced by a process comprising the steps of:
- (a) in the presence of a substance to be tested, reacting a glutamate receptor protein according to claim 1 with a substance which binds to said protein;
- (b) detecting inhibition or promotion of said reaction; and
- (c) analyzing said inhibition or promotion of said reaction by said substance to be tested, and determining whether said substance to be tested is an agonist for glutamic acid.

Finally, the inventive subject matter relates to a pharmaceutical composition comprising:
- (a) an active agent for modulating a second messenger which is generated by binding of glutamic acid to a glutamate receptor, produced by a process comprising the steps of:
  - (i) in the presence of a substance to be tested, reacting a glutamate receptor protein according to claim 1 with a substance which binds to said protein;
  - (ii) detecting inhibition or promotion of said reaction; and
  - (iii) analyzing said inhibition or promotion of said reaction by said substance to be tested, and determining whether said substance to be tested is an agonist for glutamic acid; and
- (b) a pharmaceutically acceptable carrier.

The following examples are illustrative of the inventive subject matter and are not intended to be limitations thereon. Unless otherwise indicated, all percentages are based upon 100% by weight of the final composition.

EXAMPLE 1

Cloning of Novel Metabotropic Glutamate Receptor cDNA from Circumvallate Papillae of Rat Total RNA derived from circumvallate papillae of ten rats of Wistar strain of 16 weeks age were extracted and subjected to a reverse transcription reaction to give cDNA (kit used: SuperScript, Gibco-BRL). cDNA coding for full length of mGluR1 was used as a template and a PCR was carried out by Z-Taq. This enzyme has a good replication efficiency at 3'-side and is suitable for a TOPO TA cloning reaction after that. The PCRproductwas subjected to electrophoresis using 2% agarose gel and the sequences were analyzed by an ABI Sequencer Model 3100 (ABI Co., Ltd.).

Taste mGluR1β type A was cloned from circumvallate papillae, with unique sequence at 5'-side Forward primers specific to mGluR1β type A variant cDNA prepared by Hokkaido System Science; the primers used are shown in Table 1. The following reverse primers were prepared from brain type mRNA sequence (mGluR1-4253R 5'-TAC CAT ATG GAA TTG TGC TTT GTC A-3' (SEQ ID NO: 4) and mGluR1-4198R 5'-ATA ATT CAA GAG TCA CAA TCC TGG C-3' (SEQ ID NO: 11) for type A (Masu, et al., Nature, 349:760, 1991).

cDNA (150 ng) was used as a template, then 10 μM of forward and reverse primers, 10×LA PCR buffer, 2.5 mM of $MgCl_2$ and 2.5 mM of dNTP were mixed and 0.25 units of Z-Taq enzyme was placed therein to make the total volume 10 μl. Conditions for the PCR reactions: GeneAmp PCR System 9700 was used where a cycle of 94° C. for 20 seconds, 56° C. for 1 minute and 68° C. for 3 minutes was carried out for 30 cycles; finally, 10 minute extension for 68° C. was done. Further, the second PCR was conducted and the resulting template was subjected to a cloning using pCR11-TOPO vector by a TOPO TA Cloning Kit (Invitrogen). Positive clones were subjected to a colony PCR while plasmids were purified by a Hispeed Plasmid Maxi-Kit (Quiagen) followed by subjecting to a functional analysis.

As a result, mGluR1β Type A cDNA described in SEQ ID NO: 19 was found.

TABLE 1

Primers

| Name | | | Primer Name | SEQ ID NO | Sequence |
|---|---|---|---|---|---|
| Brain mGluR1a | PCR-1 | Forward | mGluR1-50F | 21 | 5'-GAG ACC AAT AGC TGT GTC TAC CC-3' |
| | | Reverse | mGluR1-4253R | 4 | 5'-TAC CAT ATG GAA TTG TGC TTT GTC A-3' |
| | PCR-2 | Forward | mGluR1-114F | 12 | 5'-TGG ACA CCT GAT CCA CAC ACC TT-3' |
| | | Reverse | mGluR1-4198R | 11 | 5'-ATA ATT CAA GAG TCA CAA TCC TGG C-3' |
| Taste mGluR1βa | PCR-1 | Forward | mGluR1-790-1F | 22 | 5'-GGG ACT CTC TCC TGT CTT GTG AG-3' |
| | | Reverse | mGluR1-4253R | 4 | 5'-TAC CAT ATG GAA TTG TGC TTT GTC A-3' |
| | PCR-2 | Forward | mGluR1-790-2F | 23 | 5'-AGC ATA ACA GGG AAT TGC AGT GG-3' |
| | | Reverse | mGluR1-4198R | 11 | 5'-ATA ATT CAA GAG TCA CAA TCC TGG C-3' |

EXAMPLE 2

In Situ Hybridization of Stomach mGluR1

Rat stomach mucosa was prepared as described previously (Hoshino et al., 1999, and Yoshida et al., 2001). Hybridization was performed with probes at concentrations of 200-500 ng/ml in a hybridization solution (50% formamide, 5×SSC, 1% SDS, 50 µg/ml tRNA, and 50 µg/ml heparin) at 55° C. for 16 h. Antisense probes with nucleotide sequence common to all mGluR1 variants (SEQ ID NO: 17) were labeled with digoxigenin and sections incubated with anti digoxigenin alkaline phosphatase conjugate antibodies (Roche Molecular Biochemicals). Signals were developed with BM purple substrate (Roche Molecular Biochemicals).

Figure 4:
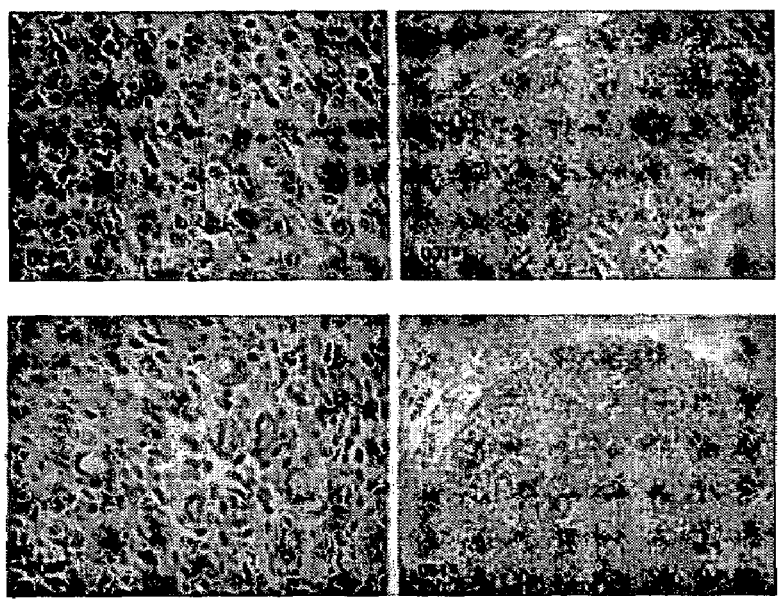
FIG. 4 is a series of photographs which shows stomach mucosa containing cells expressing mGluR1 variant. Neck mucous, chief and parietal cells hybridized with mGluR1 antisense probe at the stomach body as shown at pictures in the left panel.

As a result, in situ hybridization this analysis revealed that the stomach cells that contain mGluR1 transcripts are: neck mucous, chief and parietal cells as shown in the pictures of the left side FIG. 4 using an mGluR1 anti-sense probe.

EXAMPLE 3

Cloning of Novel Metabotropic Glutamate Receptor cDNA from Stomach of Rat

Tissue and RNA. Stomach was scraped from 20 adult (12 to 16-week old) Sprague-Dawley rats (Charles River, Japan). Rat Cerebellum was sampled to clone mGluR1a as control. Total RNA was then extracted with ISOGEN reagent (Wako, Osaka, Japan) and first-strand 5' RACE (rapid amplification of cDNA ends) synthesized using SuperScript reverse transcriptase, oligo (dT) 12-18 primer (both from Invitrogen, USA) and SMART II oligonucleotide (SMART RACE cDNA amplification kit, Clontech Laboratories, USA).

3' end PCR. The C-terminal sequence corresponding to the truncated C-terminal was determined by a series of PCR reactions. Sequence was analyzed with an ABI Sequencer Model 3100. In an intend to produce a full-length stomach variant mGluR1, two sequences were yielded by PCR combining the N-Terminal forward primer-1 [NFP-1] (5'-GGGACTCTCCTCCTGTCTTGTGAG-3'; SEQ ID NO: 3), homologous to the truncated N-terminal sequence, with C-Terminal reverse primer designed from the mGluR1a splicing variant sequence (mGluR14253R 5'-TACCATATGGAATTGTGCTTTGTCA-3'; SEQ ID NO: 4). Sequence analysis revealed that one of the sequences was identical to mGluR1a C-terminus and the other showed a unique truncation that is unlike any mGluR1 splicing variants (Soloviev at al., 1999). Both C-terminal regions were confirmed by connecting the NFP-1 forward primer with either a specific C-terminal reverse primer homologous to the truncated region (mGluR1-COOR variant 5'-TTGACACTCCTTGGTGCTGGCAT-3'; SEQ ID NO: 5) or a primer homologous only to mGluR1 type a (mGluR13241Ra 5'-GTAAAGGGTCTTGGTGCTGGCAT-3'; SEQ ID NO: 6) (FIG. 6).

Crossover PCR and cloning. After sequence analysis, the whole coding sequence of the mGluR1 stomach variant was constructed by crossover PCR using the following primers:

N-Terminal forward primer1 [NFP-1] (SEQ ID NO: 3)

5'-GGGACTCTCCTCCTGTCTTGTGAG-3'

N-Terminal reverse primer1 [NRP-1] (SEQ ID NO: 7)

5'-GTATTGTCCTCTTCTTCCACATTG-TAAAGGGTCTTGGTGCTGGCAT-3'

C-Terminal forward primer1 [CFP-2] (SEQ ID NO: 8)

5'-AATGTGGAAGAAGAGGACAATACCCCTTC-3'

C-Terminal reverse primer1 [CRP-2] (SEQ ID NO: 9)

5'-TACCATATGGAATTGTGCTTTGTCA-3'

Fragments yielded by NFP-1&NRP1 and CFP-2&CRP-2 were combined to obtained the final stomach mGluR1 cDNA variant by the next primers:

[NFP-2] 5'-AGCATAACAGGGAATTGCAGTGG-3' (SEQ ID NO: 10)

mGluR1-4198R 5'-ATAATTCAAGAGTCACAATC-CTGGC-3' (SEQ ID NO: 11)

The first amplification was performed with pfu DNA polymerase enzyme (Promega, USA) while the crossover PCR was carried out with Easy-A high-fidelity PCR cloning enzyme (Stratagene, USA).

The final template was cloned into the pcDNA3.1/V5-His vector through a TOPO cloning reaction (TOPO TA Expression Kit, Invitrogen, USA).

The forward primer used to amplify mGluR1 from rat Cerebellum as a control for functional analysis was the mGluR1-114F (5'TGGACACCTGATCCACACACCTT-3'; SEQ ID NO: 12) and the reverse primer mGluR1-4198R (SEQ ID NO: 11).

Figure 3:
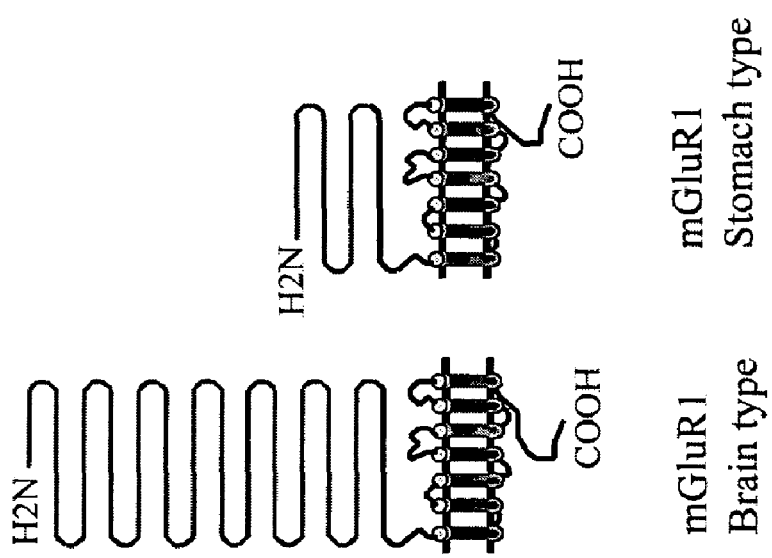
FIG. 3 is a drawing which shows an illustration comparing the brain mGluR1 with the stomach mGluR1 variant.

As a result, novel stomach type, mGluR1β cDNA described in SEQ ID NO: 1 was found. The N-terminus for stomach mGluR1 resulted to have exactly the same sequence that the one in taste tissue called mGluR1β type A variant of Example 1, which was described by Applicants in PCT Publication No. WO 03/068818. Details for the C-terminal sequence are indicated in FIG. 2. The upper panel indicates the native nucleotide sequence of brain mGluR1 type A aligned with the corresponding sequence cloned from stomach. At the upper line in capital and bold letters are the related amino acids to the brain sequence. After the splicing site the sequence in cloned stomach-mGluR1 continues with the original brain cDNA sequence further down the stop codon. This 3' end also contains a stop codon in frame with the open reading frame. The resulting receptor from stomach contains a shorter C-terminal amino acid sequence compared to the brain with 33 additional amino acids at the end specific to this variant. The different forms of the brain and stomach-mGluR1 transcripts are represented in the lower panel of FIG. 2. The discrepancy at the 3' region between both RNAs, brain and stomach, is that around 800 bases are missing in the stomach sequence. The putative protein structure for the brain and stomach-mGluR1 are shown in FIG. 3.

FIG. 1 upper panel illustrates the high homology that exists among rat, mouse and human mGluR1 amino acid sequence at the N-terminal region where taste and stomach mGluR1 protein starts being synthesized (M410 in the mouse). The homology is also compared to other glutamate (mGluR4) and taste (T1R1) receptors from the same family at the equivalent peptide sequence site. The lower panel of FIG. 1 shows the nucleotide homology between the mouse and the rat at the intron site where stomach and taste 5' cDNA for mGluR1 begins. This highly conserved amino acid sequence suggests that variant beta is likely found in others species as well. In addition, the structure described for the beta variant is maintained in the mouse 5' end.

Figure 5:
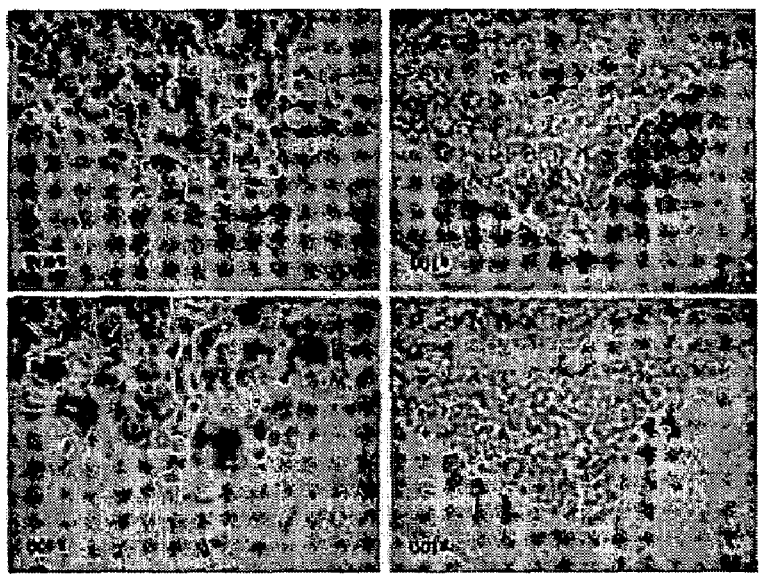
FIG. 5 is a series of photographs which shows in situ hybridization of mGluR1 variant in cerebellum control tissue. Purkinje cells from cerebellum stained in blue expresses the mGluR1 variant transcript. In the left panel, tissue sections are hybridized with an antisense probe. The right panel shows sense hybridization.
Figure 7:
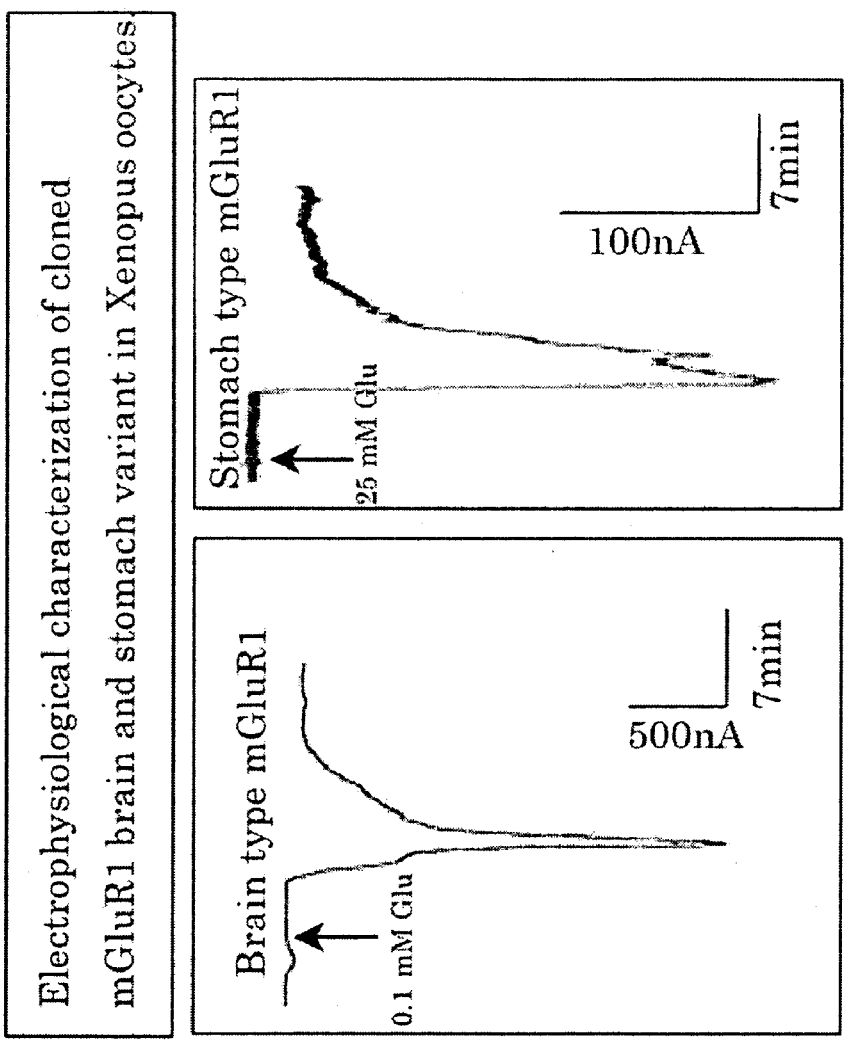
FIG. 7a is a graph which depicts changes in membrane currency when brain variant mGluR1 is expressed in oocytes of *Xenopus* and sodium glutamate is acted thereon.
FIG. 7b is a graph which depicts changes in membrane currency when stomach mGluR1 variant is expressed in oocytes of *Xenopus* and sodium glutamate is acted thereon.

To study what cells in the stomach express mGluR1 in situ hybridization was performed on stomach sections. This analysis revealed that the stomach cells that contain mGluR1 transcripts are: neck mucous, chief and parietal cells, as shown in the pictures of the left side of FIG. 4 using an mGluR1 anti-sense probe. FIG. 5 is a positive control indicating the abundant mGluR1 expression at the left site panel colored in blue in Purkinje cells from cerebellum applying the same mGluR1 anti-sense probe than that was used in the stomach.

To study its function, truncated stomach mGluR1 was synthesized by crossover PCR. The primer combination for PCR reaction as well as the final product is shown in FIG. 6. Primers were designed to specifically target the truncated region (NRP-2 and CFP-2). The full sequence cDNA was produced by linking the PCR products in a final reaction to generate the template shown in the agarose gel at the figure. Sequence analysis of the PCR end product was confirmed and used for electrophysiological studies.

EXAMPLE 3

Functional Analysis cRNA synthesis. The resulting pcDNA3.1/V5-His vector was used as a template to synthesize the corresponding stomach and brain mGluR1 cRNA. Target DNA was amplified again with pfu DNA polymerase enzyme (Promega, USA) including the T7 promoter sequence (T7 PCR Forward primer 5'-TATTTAATACGACTCACTATAG-GATAAGCATAACAGGGAATTGCAGTGG-3'; SEQ ID NO: 13) with the reverse primer mGluR1-4198R (SEQ ID NO: 11). Capped RNA was synthesized with a T7 transcription kit (mMessage mMachine, Ambion, USA). Reaction mixture was incubated for 2 hours at 37° C. for complete RNA synthesis and remaining template DNA was degraded by adding 1 mL of DNase 1 during 15 minutes. Transcripts were purified by phenol-chloroform extraction and isopropanol precipitation. cRNA was reconstituted in diethyl pyrocarbonate-treated (DEPC) water and quantitated by UV light absorbance before oocyte injection.

Oocyte injection. Twenty-four hours after collection, healthy *Xenopus* oocytes retaining clear animal and vegetal pole were injected (microinjector, WPI) with about 25 nL containing 100 ng of CRNA using a standard-bore glass capillary tube of 12 mm diameter at the tip. Electrophysiological recording was performed at 24 and 48 hours post injection in MBS buffer [88 mM NaCl, 1 mM KCl, 2.4 mM NaHCO$_3$, 10 mM HEPES, 0.82 mM MgSO$_4$, 0.33 mM Ca(NO$_3$)$_2$, 0.91 mM CaCl$_2$, pH 7.5] supplemented with 2 mM pyruvate and 0.5 mM theophylline at 18° C. (28).

Voltage-clamp. Oocytes were placed in a recording chamber and perfused with MBS at room temperature. Recording and clamping microelectrodes were pulled from 1.5 mm (outside diameter) capillary tubing filled with 3 M KCL. The electrodes were then impaled into the animal pole and voltage-clamped at −70 mV using a Geneclamp amplifier (Axon Instruments, USA). L-glutamate was perfused into the recording chamber and Ca$^{2+}$ dependent Cl$^-$ peak current in oocytes expressing rat mGluR1 recorded. Data recording and analysis was done using pClamp software (Axon Instruments, USA).

Results. Receptor activity was assessed in *Xenopus* oocytes by in vitro cRNA synthesis from full-length mGluR1 clone and posterior oocyte microinjection. The stomach variant was functionally compared with the already established response elicited by brain-mGluR1. Current responses after L-glutamate application during 30 seconds were recorded from xenopus oocytes injected with the in vitro synthesized mGluR1 cRNA for either the brain (left) or stomach (right) variant. Recordings were done under −70 mV voltage clamp Downward deflection an inward current. Both brain and stomach-mGluR1 activated a Ca$^{2+}$ dependent Cl$^-$ channel. But the brain variant achieved maximum amplitude using 100 mM L-glutamate as stimuli, while taste-mGluR1 required a much higher glutamate concentration for maximum stimulation (25 mM, in accordance with the amount found in foodstuffs). In addition, glutamate evoked a larger inward current in oocytes expressing the brain-mGluR1 opposed to oocytes bearing the stomach variant.

Figure 8:
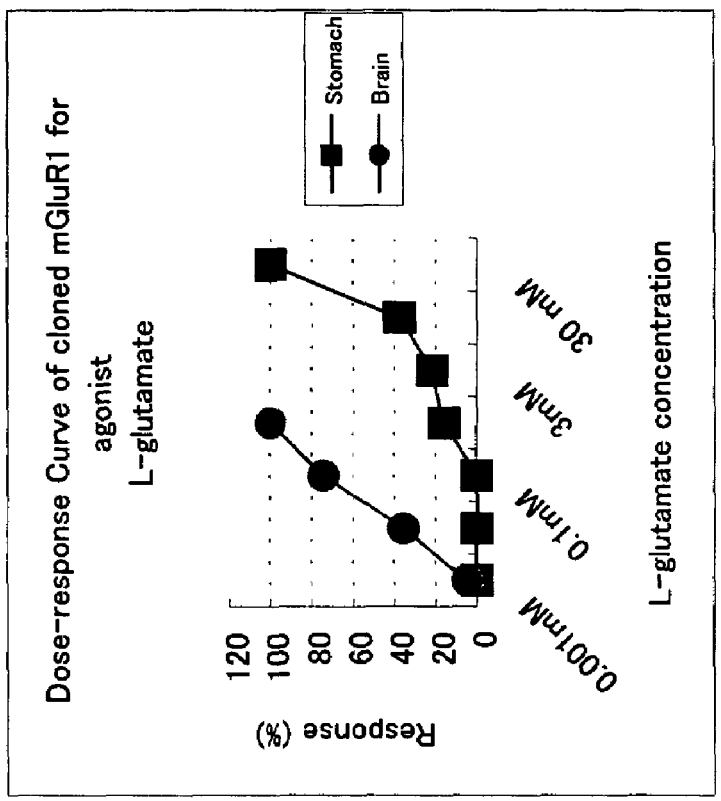
FIG. 8 is a graph which shows current responses to serial concentrations of glutamate on stomach or brain mGluR1 variant.

Current responses to serial concentrations of glutamate as stimuli were recorded from oocytes injected with either the stomach (blue) or brain (pink) variant mGluR1. Adose-response curve (FIG. 8) representing the mean of 2 to 3 sets of data from each group was produced showing that the stomach-mGluR1 has a lower affinity for its ligand than the receptor found in the brain probably due to its short N-terminal.

INDUSTRIAL APPLICABILITY

In accordance with the inventive subject matter, there is provided a novel metabotropic glutamate receptor. This glutamate receptor is able to be used for the search of agonist, antagonist or allosteric modulator for glutamic acid. It is also able to be used as a food additive as a novel umami-tasting substance and also as a drug for improving diseases and symptoms caused by metabolism abnormality in digestive tracts.

The inventive subject matter being thus described, it will be obvious that the same may be modified or varied in many ways. Such modifications and variations are not to be regarded as a departure from the spirit and scope of the inventive subject matter and all such modifications and variations are intended to be included within the scope of the following claims.

We claim:

1. An isolated DNA molecule, comprising:
 (a) a nucleic acid sequence encoding a glutamate receptor protein selected from the group consisting of:
  (A) the amino acid sequence of SEQ ID NO: 2, or
  (B) the amino acid sequence of SEQ ID NO: 2 with at least one amino acid substitution selected from the group consisting of:
   (i) His 26 to Tyr,
   (ii) Arg 39 to Ser,
   (iii) Val 51 to Ile, or
   (iv) combinations thereof;
 (b) a nucleic acid sequence of SEQ ID NO: 1;
 (c) a nucleic acid sequence of residues 442-2169 of SEQ ID NO: 1; or
 (d) a nucleic acid sequence which hybridizes with SEQ ID NO: 1 at 60° C and at a salt concentration of 0.1×SSC and 0.1% SDS.

2. A host cell transformed with an isolated DNA molecule coding for the glutamate receptor protein of claim 1 in an expressible form.

3. The cell of claim 2, wherein said isolated DNA molecule in an expressible form comprises a vector.

* * * * *

SEQUENCE LISTING

<160> NUMBER OF SEQ ID NOS: 23

<210> SEQ ID NO 1
<211> LENGTH: 2237
<212> TYPE: DNA
<213> ORGANISM: Rattus norvegicus
<220> FEATURE:
<221> NAME/KEY: CDS
<222> LOCATION: (442)..(2169)
<223> OTHER INFORMATION:

```
<220> FEATURE:
<221> NAME/KEY: misc_feature
<223> OTHER INFORMATION: mGluR1, stomach, cDNA

<400> SEQUENCE: 1
gggactctct cctgtcttgt gaggctgaag cataacaggg aattgcagtg gcttaaagta      60
gactttggct tctctggatt gctttgttta tagatatctc tgaactcatt tgtgagacac     120
tgtcttcttc ttctctcttc accccaaccc ctgcattgtt ttagtgatgg atgggcagac     180
agagatgaag tcatcgaagg ctatgaggtg gaagccaacg gagggatcac aataaagctt     240
cagtctccag aggtcaggtc atttgatgac tacttcctga agctgaggct ggacaccaac     300
acaaggaatc cttggttccc tgagttctgg caacatcgct tccagtgtcg cctacctgga     360
cacctcttgg aaaaccccaa ctttaagaaa gtgtgcacag gaaatgaaag cttggaagaa     420
aactatgtcc aggacagcaa a atg gga ttt gtc atc aat gcc atc tat gcc       471
                        Met Gly Phe Val Ile Asn Ala Ile Tyr Ala
                          1               5                  10 atg gca cat ggg ctg cag aac atg cac cat gct ctg tgt ccc ggc cat       519
Met Ala His Gly Leu Gln Asn Met His His Ala Leu Cys Pro Gly His
             15                  20                  25 gtg ggc ctg tgt gat gct atg aaa ccc att gat ggc agg aag ctc ctg       567
Val Gly Leu Cys Asp Ala Met Lys Pro Ile Asp Gly Arg Lys Leu Leu
         30                  35                  40 gat ttc ctc atc aaa tcc tct ttt gtc gga gtg tct gga gag gag gtg       615
Asp Phe Leu Ile Lys Ser Ser Phe Val Gly Val Ser Gly Glu Glu Val
     45                  50                  55 tgg ttc gat gag aag ggg gat gct ccc gga agg tat gac att atg aat       663
Trp Phe Asp Glu Lys Gly Asp Ala Pro Gly Arg Tyr Asp Ile Met Asn
 60                  65                  70 ctg cag tac aca gaa gct aat cgc tat gac tat gtc cac gtg ggg acc       711
Leu Gln Tyr Thr Glu Ala Asn Arg Tyr Asp Tyr Val His Val Gly Thr
 75                  80                  85                  90 tgg cat gaa gga gtg ctg aat att gat gat tac aaa atc cag atg aac       759
Trp His Glu Gly Val Leu Asn Ile Asp Asp Tyr Lys Ile Gln Met Asn
             95                 100                 105 aaa agc gga atg gta cga tct gtg tgc agt gag cct tgc tta aag ggt       807
Lys Ser Gly Met Val Arg Ser Val Cys Ser Glu Pro Cys Leu Lys Gly
         110                 115                 120 cag att aag gtc ata cgg aaa gga gaa gtg agc tgc tgc tgg atc tgc       855
Gln Ile Lys Val Ile Arg Lys Gly Glu Val Ser Cys Cys Trp Ile Cys
     125                 130                 135 acg gcc tgc aaa gag aat gag ttt gtg cag gac gag ttc acc tgc aga       903
Thr Ala Cys Lys Glu Asn Glu Phe Val Gln Asp Glu Phe Thr Cys Arg
 140                 145                 150 gcc tgt gac ctg ggg tgg tgg ccc aac gca gag ctc aca ggc tgt gag       951
Ala Cys Asp Leu Gly Trp Trp Pro Asn Ala Glu Leu Thr Gly Cys Glu
155                 160                 165                 170 ccc att cct gtc cgt tat ctt gag tgg agt gac ata gaa tct atc ata       999
Pro Ile Pro Val Arg Tyr Leu Glu Trp Ser Asp Ile Glu Ser Ile Ile
             175                 180                 185 gcc atc gcc ttt tct tgc ctg ggc atc ctc gtg acg ctg ttt gtc acc      1047
Ala Ile Ala Phe Ser Cys Leu Gly Ile Leu Val Thr Leu Phe Val Thr
         190                 195                 200 ctc atc ttc gtt ctg tac cgg gac aca ccc gtg gtc aaa tcc tcc agt      1095
Leu Ile Phe Val Leu Tyr Arg Asp Thr Pro Val Val Lys Ser Ser Ser
     205                 210                 215 agg gag ctc tgc tat atc att ctg gct ggt att ttc ctc ggc tat gtg      1143
Arg Glu Leu Cys Tyr Ile Ile Leu Ala Gly Ile Phe Leu Gly Tyr Val
 220                 225                 230
```

```
tgc cct ttc acc ctc atc gcc aaa cct act acc aca tcc tgc tac ctc      1191
Cys Pro Phe Thr Leu Ile Ala Lys Pro Thr Thr Thr Ser Cys Tyr Leu
235                 240                 245                 250 cag cgc ctc cta gtt ggc ctc tct tct gcc atg tgc tac tct gct tta      1239
Gln Arg Leu Leu Val Gly Leu Ser Ser Ala Met Cys Tyr Ser Ala Leu
                255                 260                 265 gtg acc aaa acc aat cgt att gca cgc atc ctg gct ggc agc aag aag      1287
Val Thr Lys Thr Asn Arg Ile Ala Arg Ile Leu Ala Gly Ser Lys Lys
            270                 275                 280 aag atc tgc acc cgg aag ccc aga ttc atg agc gct tgg gcc caa gtg      1335
Lys Ile Cys Thr Arg Lys Pro Arg Phe Met Ser Ala Trp Ala Gln Val
        285                 290                 295 atc ata gcc tcc att ctg att agt gta cag cta aca cta gtg gtg acc      1383
Ile Ile Ala Ser Ile Leu Ile Ser Val Gln Leu Thr Leu Val Val Thr
    300                 305                 310 ttg atc atc atg gag cct ccc atg ccc att ttg tcc tac ccg agt atc      1431
Leu Ile Ile Met Glu Pro Pro Met Pro Ile Leu Ser Tyr Pro Ser Ile
315                 320                 325                 330 aag gaa gtc tac ctt atc tgc aat acc agc aac ctg ggt gta gtg gcc      1479
Lys Glu Val Tyr Leu Ile Cys Asn Thr Ser Asn Leu Gly Val Val Ala
                335                 340                 345 cct gtg ggt tac aat gga ctc ctc atc atg agc tgt acc tac tat gcc      1527
Pro Val Gly Tyr Asn Gly Leu Leu Ile Met Ser Cys Thr Tyr Tyr Ala
            350                 355                 360 ttc aag acc cgc aac gtg ccg gcc aac ttc aat gag gct aaa tac atc      1575
Phe Lys Thr Arg Asn Val Pro Ala Asn Phe Asn Glu Ala Lys Tyr Ile
        365                 370                 375 gcc ttc acc atg tac act acc tgc atc atc tgg ctg gct ttc gtt ccc      1623
Ala Phe Thr Met Tyr Thr Thr Cys Ile Ile Trp Leu Ala Phe Val Pro
    380                 385                 390 att tac ttt ggg agc aac tac aag atc atc act acc tgc ttc gcg gtg      1671
Ile Tyr Phe Gly Ser Asn Tyr Lys Ile Ile Thr Thr Cys Phe Ala Val
395                 400                 405                 410 agc ctc agt gtg acg gtg gcc ctg ggg tgc atg ttt act ccg aag atg      1719
Ser Leu Ser Val Thr Val Ala Leu Gly Cys Met Phe Thr Pro Lys Met
                415                 420                 425 tac atc atc att gcc aaa cct gag agg aac gtc cgc agt gcc ttc acg      1767
Tyr Ile Ile Ile Ala Lys Pro Glu Arg Asn Val Arg Ser Ala Phe Thr
            430                 435                 440 acc tct gat gtt gtc cgc atg cac gtc ggt gat ggc aaa ctg ccg tgc      1815
Thr Ser Asp Val Val Arg Met His Val Gly Asp Gly Lys Leu Pro Cys
        445                 450                 455 cgc tcc aac acc ttc ctc aac att ttc cgg aga aag aag ccc ggg gca      1863
Arg Ser Asn Thr Phe Leu Asn Ile Phe Arg Arg Lys Lys Pro Gly Ala
    460                 465                 470 ggg aat gcc aat tct aac ggc aag tct gtg tca tgg tct gaa cca ggt      1911
Gly Asn Ala Asn Ser Asn Gly Lys Ser Val Ser Trp Ser Glu Pro Gly
475                 480                 485                 490 gga aga cag gcg ccc aag gga cag cac gtg tgg cag cgc ctc tct gtg      1959
Gly Arg Gln Ala Pro Lys Gly Gln His Val Trp Gln Arg Leu Ser Val
                495                 500                 505 cac gtg aag acc aac gag acg gcc tgt aac caa aca gcc gta atc aaa      2007
His Val Lys Thr Asn Glu Thr Ala Cys Asn Gln Thr Ala Val Ile Lys
            510                 515                 520 ccc ctc act aaa agt tac caa ggc tct ggc aag agc ctg acc ttt tca      2055
Pro Leu Thr Lys Ser Tyr Gln Gly Ser Gly Lys Ser Leu Thr Phe Ser
        525                 530                 535 gat gcc agc acc aag gag tgt caa ccc ttc cag aaa tgt gta gaa agc      2103
Asp Ala Ser Thr Lys Glu Cys Gln Pro Phe Gln Lys Cys Val Glu Ser
```

```
                  540                 545                 550
agg gtg agg gat ggg gat gga gga cca cgg tct gca ggg aag aaa aaa        2151
Arg Val Arg Asp Gly Asp Gly Gly Pro Arg Ser Ala Gly Lys Lys Lys
555                 560                 565                 570 aaa atg ctg cgg ctg cct taaagaagga gagggacgat gccaactgaa              2199
Lys Met Leu Arg Leu Pro
                575 cagtggtcct ggccaggatt gtgactcttg aattattc                             2237
```

<210> SEQ ID NO 2
<211> LENGTH: 576
<212> TYPE: PRT
<213> ORGANISM: Rattus norvegicus

<400> SEQUENCE: 2

```
Met Gly Phe Val Ile Asn Ala Ile Tyr Ala Met Ala His Gly Leu Gln
1               5                   10                  15

Asn Met His His Ala Leu Cys Pro Gly His Val Gly Leu Cys Asp Ala
                20                  25                  30

Met Lys Pro Ile Asp Gly Arg Lys Leu Leu Asp Phe Leu Ile Lys Ser
            35                  40                  45

Ser Phe Val Gly Val Ser Gly Glu Glu Val Trp Phe Asp Glu Lys Gly
        50                  55                  60

Asp Ala Pro Gly Arg Tyr Asp Ile Met Asn Leu Gln Tyr Thr Glu Ala
65                  70                  75                  80

Asn Arg Tyr Asp Tyr Val His Val Gly Thr Trp His Glu Gly Val Leu
                85                  90                  95

Asn Ile Asp Asp Tyr Lys Ile Gln Met Asn Lys Ser Gly Met Val Arg
            100                 105                 110

Ser Val Cys Ser Glu Pro Cys Leu Lys Gly Gln Ile Lys Val Ile Arg
        115                 120                 125

Lys Gly Glu Val Ser Cys Cys Trp Ile Cys Thr Ala Cys Lys Glu Asn
130                 135                 140

Glu Phe Val Gln Asp Glu Phe Thr Cys Arg Ala Cys Asp Leu Gly Trp
145                 150                 155                 160

Trp Pro Asn Ala Glu Leu Thr Gly Cys Glu Pro Ile Pro Val Arg Tyr
                165                 170                 175

Leu Glu Trp Ser Asp Ile Glu Ser Ile Ile Ala Ile Ala Phe Ser Cys
            180                 185                 190

Leu Gly Ile Leu Val Thr Leu Phe Val Thr Leu Ile Phe Val Leu Tyr
        195                 200                 205

Arg Asp Thr Pro Val Val Lys Ser Ser Ser Arg Glu Leu Cys Tyr Ile
210                 215                 220

Ile Leu Ala Gly Ile Phe Leu Gly Tyr Val Cys Pro Phe Thr Leu Ile
225                 230                 235                 240

Ala Lys Pro Thr Thr Thr Ser Cys Tyr Leu Gln Arg Leu Leu Val Gly
                245                 250                 255

Leu Ser Ser Ala Met Cys Tyr Ser Ala Leu Val Thr Lys Thr Asn Arg
            260                 265                 270

Ile Ala Arg Ile Leu Ala Gly Ser Lys Lys Lys Ile Cys Thr Arg Lys
        275                 280                 285

Pro Arg Phe Met Ser Ala Trp Ala Gln Val Ile Ile Ala Ser Ile Leu
290                 295                 300

Ile Ser Val Gln Leu Thr Leu Val Val Thr Leu Ile Ile Met Glu Pro
305                 310                 315                 320
```

```
Pro Met Pro Ile Leu Ser Tyr Pro Ser Ile Lys Glu Val Tyr Leu Ile
            325                 330                 335

Cys Asn Thr Ser Asn Leu Gly Val Val Ala Pro Val Gly Tyr Asn Gly
            340                 345                 350

Leu Leu Ile Met Ser Cys Thr Tyr Tyr Ala Phe Lys Thr Arg Asn Val
            355                 360                 365

Pro Ala Asn Phe Asn Glu Ala Lys Tyr Ile Ala Phe Thr Met Tyr Thr
        370                 375                 380

Thr Cys Ile Ile Trp Leu Ala Phe Val Pro Ile Tyr Phe Gly Ser Asn
385                 390                 395                 400

Tyr Lys Ile Ile Thr Thr Cys Phe Ala Val Ser Leu Ser Val Thr Val
            405                 410                 415

Ala Leu Gly Cys Met Phe Thr Pro Lys Met Tyr Ile Ile Ile Ala Lys
            420                 425                 430

Pro Glu Arg Asn Val Arg Ser Ala Phe Thr Thr Ser Asp Val Val Arg
            435                 440                 445

Met His Val Gly Asp Gly Lys Leu Pro Cys Arg Ser Asn Thr Phe Leu
            450                 455                 460

Asn Ile Phe Arg Arg Lys Lys Pro Gly Ala Gly Asn Ala Asn Ser Asn
465                 470                 475                 480

Gly Lys Ser Val Ser Trp Ser Glu Pro Gly Gly Arg Gln Ala Pro Lys
                485                 490                 495

Gly Gln His Val Trp Gln Arg Leu Ser Val His Val Lys Thr Asn Glu
            500                 505                 510

Thr Ala Cys Asn Gln Thr Ala Val Ile Lys Pro Leu Thr Lys Ser Tyr
            515                 520                 525

Gln Gly Ser Gly Lys Ser Leu Thr Phe Ser Asp Ala Ser Thr Lys Glu
            530                 535                 540

Cys Gln Pro Phe Gln Lys Cys Val Glu Ser Arg Val Arg Asp Gly Asp
545                 550                 555                 560

Gly Gly Pro Arg Ser Ala Gly Lys Lys Lys Met Leu Arg Leu Pro
                565                 570                 575
```

<210> SEQ ID NO 3
<211> LENGTH: 23
<212> TYPE: DNA
<213> ORGANISM: Artificial
<220> FEATURE:
<223> OTHER INFORMATION: primer, NFP-1

<400> SEQUENCE: 3
gggactctct cctgtcttgt gag         23

<210> SEQ ID NO 4
<211> LENGTH: 25
<212> TYPE: DNA
<213> ORGANISM: Artificial
<220> FEATURE:
<223> OTHER INFORMATION: primer, mGluR1-4253R

<400> SEQUENCE: 4
taccatatgg aattgtgctt tgtca         25

<210> SEQ ID NO 5
<211> LENGTH: 23
<212> TYPE: DNA
<213> ORGANISM: Artificial
<220> FEATURE:

<223> OTHER INFORMATION: primer, mGluR1-COOR

<400> SEQUENCE: 5
ttgacactcc ttggtgctgg cat                                    23

<210> SEQ ID NO 6
<211> LENGTH: 23
<212> TYPE: DNA
<213> ORGANISM: Artificial
<220> FEATURE:
<223> OTHER INFORMATION: primer, mGluR1-3241Ra

<400> SEQUENCE: 6
gtaaagggtc ttggtgctgg cat                                    23

<210> SEQ ID NO 7
<211> LENGTH: 46
<212> TYPE: DNA
<213> ORGANISM: Artificial
<220> FEATURE:
<223> OTHER INFORMATION: primer, NRP-1

<400> SEQUENCE: 7
gtattgtcct cttcttccac attgtaaagg gtcttggtgc tggcat           46

<210> SEQ ID NO 8
<211> LENGTH: 30
<212> TYPE: DNA
<213> ORGANISM: Artificial
<220> FEATURE:
<223> OTHER INFORMATION: primer, CFP-2

<400> SEQUENCE: 8
aatgtggaag aagaggacaa taccccttct                             30

<210> SEQ ID NO 9
<211> LENGTH: 25
<212> TYPE: DNA
<213> ORGANISM: Artificial
<220> FEATURE:
<223> OTHER INFORMATION: primer, CRP-2

<400> SEQUENCE: 9
taccatatgg aattgtgctt tgtca                                  25

<210> SEQ ID NO 10
<211> LENGTH: 23
<212> TYPE: DNA
<213> ORGANISM: Artificial
<220> FEATURE:
<223> OTHER INFORMATION: primer, NFP-2

<400> SEQUENCE: 10
agcataacag ggaattgcag tgg                                    23

<210> SEQ ID NO 11
<211> LENGTH: 25
<212> TYPE: DNA
<213> ORGANISM: Artificial
<220> FEATURE:
<223> OTHER INFORMATION: primer, mGluR1-4198R

<400> SEQUENCE: 11
ataattcaag agtcacaatc ctggc                                  25

```
<210> SEQ ID NO 12
<211> LENGTH: 23
<212> TYPE: DNA
<213> ORGANISM: Artificial
<220> FEATURE:
<223> OTHER INFORMATION: primer, mGluR1-114F

<400> SEQUENCE: 12
tggacacctg atccacacac ctt                                            23

<210> SEQ ID NO 13
<211> LENGTH: 49
<212> TYPE: DNA
<213> ORGANISM: Artificial
<220> FEATURE:
<223> OTHER INFORMATION: primer, T7 PCR Forward

<400> SEQUENCE: 13
tatttaatac gactcactat aggataagca taacagggaa ttgcagtgg                49

<210> SEQ ID NO 14
<211> LENGTH: 6820
<212> TYPE: DNA
<213> ORGANISM: Rattus norvegicus
<220> FEATURE:
<221> NAME/KEY: CDS
<222> LOCATION: (377)..(3976)
<223> OTHER INFORMATION:
<220> FEATURE:
<221> NAME/KEY: misc_feature
<223> OTHER INFORMATION: brain mGluR1 cDNA

<400> SEQUENCE: 14
```

| | | |
|---|---|---|
| ccgagaacgg ctgcagtcct ctgacctgag accaatagct gtgtctaccc ggactcagcg | 60 |
| tccagctcac cgccactaac gcgccgcgca ttggacacct gatccacaca ccttcgggca | 120 |
| ccagtgaaaa accgcgactt gattttctgg aagaacgccc ccagggtgtg ggagcggtcg | 180 |
| tggaggacca gcaggaggaa gcggagggga gaggggcagt agtggaggca gagaaagcgt | 240 |
| tgaaccagct gtgttggccg aaggcacgaa acggcaaaag gcagcggtga gcatctgtgt | 300 |
| ggttcccgct gggaacctgc aggcaggacc ggcgtgggaa cgtggctggc cgcggtgga | 360 |

```
ccgcgtcttc gccaca atg gtc cgg ctc ctc ttg att ttc ttc cca atg atc       412
               Met Val Arg Leu Leu Leu Ile Phe Phe Pro Met Ile
                 1               5                  10 ttt ttg gag atg tcc att ttg ccc agg atg cct gac aga aaa gta ttg         460
Phe Leu Glu Met Ser Ile Leu Pro Arg Met Pro Asp Arg Lys Val Leu
         15                  20                  25 ctg gca ggt gcc tcg tcc cag cgc tcc gtg gcg aga atg gac gga gat         508
Leu Ala Gly Ala Ser Ser Gln Arg Ser Val Ala Arg Met Asp Gly Asp
 30                  35                  40 gtc atc atc gga gcc ctc ttc tca gtc cat cac cag cct cca gcc gag         556
Val Ile Ile Gly Ala Leu Phe Ser Val His His Gln Pro Pro Ala Glu
 45                  50                  55                  60 aag gta ccc gaa agg aag tgt ggg gag atc agg gaa cag tat ggt atc         604
Lys Val Pro Glu Arg Lys Cys Gly Glu Ile Arg Glu Gln Tyr Gly Ile
                 65                  70                  75 cag agg gtg gag gcc atg ttc cac acg ttg gat aag att aac gcg gac         652
Gln Arg Val Glu Ala Met Phe His Thr Leu Asp Lys Ile Asn Ala Asp
             80                  85                  90 ccg gtg ctc ctg ccc aac atc act ctg ggc agt gag atc cgg gac tcc         700
Pro Val Leu Leu Pro Asn Ile Thr Leu Gly Ser Glu Ile Arg Asp Ser
         95                 100                 105 tgc tgg cac tct tca gtg gct ctc gaa cag agc atc gaa ttc atc aga         748
```

-continued

```
            Cys Trp His Ser Ser Val Ala Leu Glu Gln Ser Ile Glu Phe Ile Arg
                110                 115                 120 gac tcc ctg att tcc atc cga gat gag aag gat ggg ctg aac cga tgc        796
Asp Ser Leu Ile Ser Ile Arg Asp Glu Lys Asp Gly Leu Asn Arg Cys
125                 130                 135                 140 ctg cct gat ggc cag acc ctg ccc cct ggc agg act aag aag cct att        844
Leu Pro Asp Gly Gln Thr Leu Pro Pro Gly Arg Thr Lys Lys Pro Ile
                145                 150                 155 gct gga gtg atc ggc cct ggc tcc agc tct gtg gcc att caa gtc cag        892
Ala Gly Val Ile Gly Pro Gly Ser Ser Ser Val Ala Ile Gln Val Gln
            160                 165                 170 aat ctt ctc cag ctg ttc gac atc cca cag atc gcc tat tct gcc aca        940
Asn Leu Leu Gln Leu Phe Asp Ile Pro Gln Ile Ala Tyr Ser Ala Thr
        175                 180                 185 agc ata gac ctg agt gac aaa act ttg tac aaa tac ttc ctg agg gtg        988
Ser Ile Asp Leu Ser Asp Lys Thr Leu Tyr Lys Tyr Phe Leu Arg Val
        190                 195                 200 gtc cct tct gac act ttg cag gca agg gcg atg ctc gac ata gtc aag       1036
Val Pro Ser Asp Thr Leu Gln Ala Arg Ala Met Leu Asp Ile Val Lys
205                 210                 215                 220 cgt tac aac tgg acc tat gtc tca gca gtc cac aca gaa ggg aat tac       1084
Arg Tyr Asn Trp Thr Tyr Val Ser Ala Val His Thr Glu Gly Asn Tyr
                225                 230                 235 ggc gag agt gga atg gat gct ttc aaa gaa ctg gct gcc cag gaa ggc       1132
Gly Glu Ser Gly Met Asp Ala Phe Lys Glu Leu Ala Ala Gln Glu Gly
            240                 245                 250 ctc tgc atc gca cac tcg gac aaa atc tac agc aat gct ggc gag aag       1180
Leu Cys Ile Ala His Ser Asp Lys Ile Tyr Ser Asn Ala Gly Glu Lys
        255                 260                 265 agc ttt gac cgg ctc ctg cgt aaa ctc cgg gag cgg ctt ccc aag gcc       1228
Ser Phe Asp Arg Leu Leu Arg Lys Leu Arg Glu Arg Leu Pro Lys Ala
        270                 275                 280 agg gtt gtg gtc tgc ttc tgc gag ggc atg aca gtg cgg ggc tta ctg       1276
Arg Val Val Val Cys Phe Cys Glu Gly Met Thr Val Arg Gly Leu Leu
285                 290                 295                 300 agt gcc atg cgc cgc ctg ggc gtc gtg ggc gag ttc tca ctc att gga       1324
Ser Ala Met Arg Arg Leu Gly Val Val Gly Glu Phe Ser Leu Ile Gly
                305                 310                 315 agt gat gga tgg gca gac aga gat gaa gtc atc gaa ggc tat gag gtg       1372
Ser Asp Gly Trp Ala Asp Arg Asp Glu Val Ile Glu Gly Tyr Glu Val
            320                 325                 330 gaa gcc aac gga ggg atc aca ata aag ctt cag tct cca gag gtc agg       1420
Glu Ala Asn Gly Gly Ile Thr Ile Lys Leu Gln Ser Pro Glu Val Arg
        335                 340                 345 tca ttt gat gac tac ttc ctg aag ctg agg ctg gac acc aac aca agg       1468
Ser Phe Asp Asp Tyr Phe Leu Lys Leu Arg Leu Asp Thr Asn Thr Arg
        350                 355                 360 aat cct tgg ttc cct gag ttc tgg caa cat cgc ttc cag tgt cgc cta       1516
Asn Pro Trp Phe Pro Glu Phe Trp Gln His Arg Phe Gln Cys Arg Leu
365                 370                 375                 380 cct gga cac ctc ttg gaa aac ccc aac ttt aag aaa gtg tgc aca gga       1564
Pro Gly His Leu Leu Glu Asn Pro Asn Phe Lys Lys Val Cys Thr Gly
                385                 390                 395 aat gaa agc ttg gaa gaa aac tat gtc cag gac agc aaa atg gga ttt       1612
Asn Glu Ser Leu Glu Glu Asn Tyr Val Gln Asp Ser Lys Met Gly Phe
            400                 405                 410 gtc atc aat gcc atc tat gcc atg gca cat ggg ctg cag aac atg cac       1660
Val Ile Asn Ala Ile Tyr Ala Met Ala His Gly Leu Gln Asn Met His
        415                 420                 425
```

-continued

| | | |
|---|---|---|
| cat gct ctg tgt ccc ggc cat gtg ggc ctg tgt gat gct atg aaa ccc<br>His Ala Leu Cys Pro Gly His Val Gly Leu Cys Asp Ala Met Lys Pro<br>430                                      435                           440 | 1708 |
| att gat ggc agg aag ctc ctg gat ttc ctc atc aaa tcc tct ttt gtc<br>Ile Asp Gly Arg Lys Leu Leu Asp Phe Leu Ile Lys Ser Ser Phe Val<br>445                         450                       455                   460 | 1756 |
| gga gtg tct gga gag gag gtg tgg ttc gat gag aag ggg gat gct ccc<br>Gly Val Ser Gly Glu Glu Val Trp Phe Asp Glu Lys Gly Asp Ala Pro<br>                          465                   470                      475 | 1804 |
| gga agg tat gac att atg aat ctg cag tac aca gaa gct aat cgc tat<br>Gly Arg Tyr Asp Ile Met Asn Leu Gln Tyr Thr Glu Ala Asn Arg Tyr<br>                 480                       485                   490 | 1852 |
| gac tat gtc cac gtg ggg acc tgg cat gaa gga gtg ctg aat att gat<br>Asp Tyr Val His Val Gly Thr Trp His Glu Gly Val Leu Asn Ile Asp<br>             495                     500                   505 | 1900 |
| gat tac aaa atc cag atg aac aaa agc gga atg gta cga tct gtg tgc<br>Asp Tyr Lys Ile Gln Met Asn Lys Ser Gly Met Val Arg Ser Val Cys<br>510                                     515                   520 | 1948 |
| agt gag cct tgc tta aag ggt cag att aag gtc ata cgg aaa gga gaa<br>Ser Glu Pro Cys Leu Lys Gly Gln Ile Lys Val Ile Arg Lys Gly Glu<br>525                       530                      535                   540 | 1996 |
| gtg agc tgc tgc tgg atc tgc acg gcc tgc aaa gag aat gag ttt gtg<br>Val Ser Cys Cys Trp Ile Cys Thr Ala Cys Lys Glu Asn Glu Phe Val<br>                         545                       550                   555 | 2044 |
| cag gac gag ttc acc tgc aga gcc tgt gac ctg ggg tgg tgg ccc aac<br>Gln Asp Glu Phe Thr Cys Arg Ala Cys Asp Leu Gly Trp Trp Pro Asn<br>                    560                       565                   570 | 2092 |
| gca gag ctc aca ggc tgt gag ccc att cct gtc cgt tat ctt gag tgg<br>Ala Glu Leu Thr Gly Cys Glu Pro Ile Pro Val Arg Tyr Leu Glu Trp<br>             575                     580                   585 | 2140 |
| agt gac ata gaa tct atc ata gcc atc gcc ttt tct tgc ctg ggc atc<br>Ser Asp Ile Glu Ser Ile Ile Ala Ile Ala Phe Ser Cys Leu Gly Ile<br>590                                     595                   600 | 2188 |
| ctc gtg acg ctg ttt gtc acc ctc atc ttc gtt ctg tac cgg gac aca<br>Leu Val Thr Leu Phe Val Thr Leu Ile Phe Val Leu Tyr Arg Asp Thr<br>605                       610                      615                   620 | 2236 |
| ccc gtg gtc aaa tcc tcc agt agg gag ctc tgc tat atc att ctg gct<br>Pro Val Val Lys Ser Ser Ser Arg Glu Leu Cys Tyr Ile Ile Leu Ala<br>                   625                      630                   635 | 2284 |
| ggt att ttc ctc ggc tat gtg tgc cct ttc acc ctc atc gcc aaa cct<br>Gly Ile Phe Leu Gly Tyr Val Cys Pro Phe Thr Leu Ile Ala Lys Pro<br>             640                     645                   650 | 2332 |
| act acc aca tcc tgc tac ctc cag cgc ctc cta gtt ggc ctc tct tct<br>Thr Thr Thr Ser Cys Tyr Leu Gln Arg Leu Leu Val Gly Leu Ser Ser<br>                 655                      660                   665 | 2380 |
| gcc atg tgc tac tct gct tta gtg acc aaa acc aat cgt att gca cgc<br>Ala Met Cys Tyr Ser Ala Leu Val Thr Lys Thr Asn Arg Ile Ala Arg<br>670                                     675                   680 | 2428 |
| atc ctg gct ggc agc aag aag aag atc tgc acc cgg aag ccc aga ttc<br>Ile Leu Ala Gly Ser Lys Lys Lys Ile Cys Thr Arg Lys Pro Arg Phe<br>685                       690                      695                   700 | 2476 |
| atg agc gct tgg gcc caa gtg atc ata gcc tcc att ctg att agt gta<br>Met Ser Ala Trp Ala Gln Val Ile Ile Ala Ser Ile Leu Ile Ser Val<br>                   705                      710                   715 | 2524 |
| cag cta aca cta gtg gtg acc ttg atc atc atg gag cct ccc atg ccc<br>Gln Leu Thr Leu Val Val Thr Leu Ile Ile Met Glu Pro Pro Met Pro<br>             720                     725                   730 | 2572 |
| att ttg tcc tac ccg agt atc aag gaa gtc tac ctt atc tgc aat acc<br>Ile Leu Ser Tyr Pro Ser Ile Lys Glu Val Tyr Leu Ile Cys Asn Thr<br>                   735                      740                   745 | 2620 |

-continued

| | | |
|---|---|---|
| agc aac ctg ggt gta gtg gcc cct gtg ggt tac aat gga ctc ctc atc<br>Ser Asn Leu Gly Val Val Ala Pro Val Gly Tyr Asn Gly Leu Leu Ile<br>750                        755                      760 | | 2668 |
| atg agc tgt acc tac tat gcc ttc aag acc cgc aac gtg ccg gcc aac<br>Met Ser Cys Thr Tyr Tyr Ala Phe Lys Thr Arg Asn Val Pro Ala Asn<br>765                        770                      775                      780 | | 2716 |
| ttc aat gag gct aaa tac atc gcc ttc acc atg tac act acc tgc atc<br>Phe Asn Glu Ala Lys Tyr Ile Ala Phe Thr Met Tyr Thr Thr Cys Ile<br>                      785                      790                      795 | | 2764 |
| atc tgg ctg gct ttc gtt ccc att tac ttt ggg agc aac tac aag atc<br>Ile Trp Leu Ala Phe Val Pro Ile Tyr Phe Gly Ser Asn Tyr Lys Ile<br>                800                      805                      810 | | 2812 |
| atc act acc tgc ttc gcg gtg agc ctc agt gtg acg gtg gcc ctg ggg<br>Ile Thr Thr Cys Phe Ala Val Ser Leu Ser Val Thr Val Ala Leu Gly<br>                      815                      820                      825 | | 2860 |
| tgc atg ttt act ccg aag atg tac atc atc att gcc aaa cct gag agg<br>Cys Met Phe Thr Pro Lys Met Tyr Ile Ile Ile Ala Lys Pro Glu Arg<br>830                        835                      840 | | 2908 |
| aac gtc cgc agt gcc ttc acg acc tct gat gtt gtc cgc atg cac gtc<br>Asn Val Arg Ser Ala Phe Thr Thr Ser Asp Val Val Arg Met His Val<br>845                        850                      855                      860 | | 2956 |
| ggt gat ggc aaa ctg ccg tgc cgc tcc aac acc ttc ctc aac att ttc<br>Gly Asp Gly Lys Leu Pro Cys Arg Ser Asn Thr Phe Leu Asn Ile Phe<br>                      865                      870                      875 | | 3004 |
| cgg aga aag aag ccc ggg gca ggg aat gcc aat tct aac ggc aag tct<br>Arg Arg Lys Lys Pro Gly Ala Gly Asn Ala Asn Ser Asn Gly Lys Ser<br>                880                      885                      890 | | 3052 |
| gtg tca tgg tct gaa cca ggt gga aga cag gcg ccc aag gga cag cac<br>Val Ser Trp Ser Glu Pro Gly Gly Arg Gln Ala Pro Lys Gly Gln His<br>                      895                      900                      905 | | 3100 |
| gtg tgg cag cgc ctc tct gtg cac gtg aag acc aac gag acg gcc tgt<br>Val Trp Gln Arg Leu Ser Val His Val Lys Thr Asn Glu Thr Ala Cys<br>910                        915                      920 | | 3148 |
| aac caa aca gcc gta atc aaa ccc ctc act aaa agt tac caa ggc tct<br>Asn Gln Thr Ala Val Ile Lys Pro Leu Thr Lys Ser Tyr Gln Gly Ser<br>925                        930                      935                      940 | | 3196 |
| ggc aag agc ctg acc ttt tca gat gcc agc acc aag acc ctt tac aat<br>Gly Lys Ser Leu Thr Phe Ser Asp Ala Ser Thr Lys Thr Leu Tyr Asn<br>                      945                      950                      955 | | 3244 |
| gtg gaa gaa gag gac aat acc cct tct gct cac ttc agc cct ccc agc<br>Val Glu Glu Glu Asp Asn Thr Pro Ser Ala His Phe Ser Pro Pro Ser<br>                      960                      965                      970 | | 3292 |
| agc cct tct atg gtg gtg cac cga cgc ggg cca ccc gtg gcc acc aca<br>Ser Pro Ser Met Val Val His Arg Arg Gly Pro Pro Val Ala Thr Thr<br>                975                      980                      985 | | 3340 |
| cca cct ctg cca ccc cat ctg acc gca gaa gag acc ccc ctg ttc ctg<br>Pro Pro Leu Pro Pro His Leu Thr Ala Glu Glu Thr   Pro Leu Phe Leu<br>990                        995                      1000 | | 3388 |
| gct gat tcc gtc atc ccc aag ggc ttg cct cct cct ctc ccg cag<br>Ala Asp Ser Val Ile Pro Lys Gly Leu Pro Pro Pro Leu Pro Gln<br>1005                      1010                    1015 | | 3433 |
| cag cag cca cag cag ccg ccc cct cag cag ccc ccg cag cag ccc<br>Gln Gln Pro Gln Gln Pro Pro Pro Gln Gln Pro Pro Gln Gln Pro<br>1020                      1025                    1030 | | 3478 |
| aag tcc ctg atg gac cag ctg caa ggc gta gtc acc aac ttc ggt<br>Lys Ser Leu Met Asp Gln Leu Gln Gly Val Val Thr Asn Phe Gly<br>1035                      1040                    1045 | | 3523 |
| tcg ggg att cca gat ttc cat gcg gtg ctg gca ggc ccg ggg aca<br>Ser Gly Ile Pro Asp Phe His Ala Val Leu Ala Gly Pro Gly Thr | | 3568 |

-continued

| | | | | | | | | | | | | | | |
|---|---|---|---|---|---|---|---|---|---|---|---|---|---|---|
| 1050 | | | | | 1055 | | | | | 1060 | | | | |
| cca | gga | aac | agc | ctg | cgc | tct | ctg | tac | ccg | ccc | ccg | cct | ccg | ccg | 3613 |
| Pro | Gly | Asn | Ser | Leu | Arg | Ser | Leu | Tyr | Pro | Pro | Pro | Pro | Pro | Pro | |
| 1065 | | | | | 1070 | | | | | 1075 | | | | |
| caa | cac | ctg | cag | atg | ctg | ccc | ctg | cac | ctg | agc | acc | ttc | cag | gag | 3658 |
| Gln | His | Leu | Gln | Met | Leu | Pro | Leu | His | Leu | Ser | Thr | Phe | Gln | Glu | |
| 1080 | | | | | 1085 | | | | | 1090 | | | | |
| gag | tcc | atc | tcc | cct | cct | ggg | gag | gac | atc | gat | gat | gac | agt | gag | 3703 |
| Glu | Ser | Ile | Ser | Pro | Pro | Gly | Glu | Asp | Ile | Asp | Asp | Asp | Ser | Glu | |
| 1095 | | | | | 1100 | | | | | 1105 | | | | |
| aga | ttc | aag | ctc | ctg | cag | gag | ttc | gtg | tac | gag | cgc | gaa | ggg | aac | 3748 |
| Arg | Phe | Lys | Leu | Leu | Gln | Glu | Phe | Val | Tyr | Glu | Arg | Glu | Gly | Asn | |
| 1110 | | | | | 1115 | | | | | 1120 | | | | |
| acc | gaa | gaa | gat | gaa | ttg | gaa | gag | gag | gag | gac | ctg | ccc | aca | gcc | 3793 |
| Thr | Glu | Glu | Asp | Glu | Leu | Glu | Glu | Glu | Glu | Asp | Leu | Pro | Thr | Ala | |
| 1125 | | | | | 1130 | | | | | 1135 | | | | |
| agc | aag | ctg | acc | cct | gag | gat | tct | cct | gcc | ctg | acg | cct | cct | tct | 3838 |
| Ser | Lys | Leu | Thr | Pro | Glu | Asp | Ser | Pro | Ala | Leu | Thr | Pro | Pro | Ser | |
| 1140 | | | | | 1145 | | | | | 1150 | | | | |
| cct | ttc | cga | gat | tcc | gtg | gcc | tct | ggc | agc | tca | gtg | ccc | agt | tcc | 3883 |
| Pro | Phe | Arg | Asp | Ser | Val | Ala | Ser | Gly | Ser | Ser | Val | Pro | Ser | Ser | |
| 1155 | | | | | 1160 | | | | | 1165 | | | | |
| ccc | gta | tct | gag | tcg | gtc | ctc | tgc | acc | cct | cca | aat | gta | acc | tac | 3928 |
| Pro | Val | Ser | Glu | Ser | Val | Leu | Cys | Thr | Pro | Pro | Asn | Val | Thr | Tyr | |
| 1170 | | | | | 1175 | | | | | 1180 | | | | |
| gcc | tct | gtc | att | ctg | agg | gac | tac | aag | caa | agc | tct | tcc | acc | ctg | 3973 |
| Ala | Ser | Val | Ile | Leu | Arg | Asp | Tyr | Lys | Gln | Ser | Ser | Ser | Thr | Leu | |
| 1185 | | | | | 1190 | | | | | 1195 | | | | |

```
tag tgtgtgtgtg tgtgtggggg cggggggagt gcgcatggag aagccagaga        4026
tgccaaggag tgtcaaccct tccagaaatg tgtagaaagc agggtgaggg atggggatgg  4086
aggaccacgg tctgcaggga agaaaaaaaa aatgctgcgg ctgccttaaa gaaggagagg  4146
gacgatgcca actgaacagt ggtcctggcc aggattgtga ctcttgaatt attcaaaaac  4206
cttctctaga aagaagggga attatgacaa agcacaattc catatggtat gtaactttta  4266
tcgaaaaaaa taataaaacg taaaatataa atcaacaaaa ataatctctt cttttgctca  4326
atcgtgcata catatatctg cccacactcc cgtggtaaaa ctagaagcga agcaggccct  4386
gcgatggtgc caactgaatc ctaagttcat catcctagtg agcagatgga gagagggcag  4446
gaggcggggg taggttcgga caacagctcc catctcagac cttgactgtg ctgagtcttc  4506
agactcctgg actaaggaag acccggggac tgaccttatg agggtccctt tccactgctg  4566
tgatccattg ccagcctgta gtcacccggg ataaaggcac agtaaccttt tgcattcctg  4626
tgattccctg tgtttaagga aaaggaaagt atgagcaaag ctatcaccaa aaagagcgcc  4686
attagaagtt acgggggaga aaaaagagaa agcaagatga tatataagca cagggccttg  4746
aacaaggtga gcgtgcttca cagattccgt attaatgtac agatactttt ggagaggaga  4806
aagataacaa ggagtgtcag gccgtttgtg aactcacttg cactgtgcca accaggttct  4866
ccgctgccct tcagcaaaag aggacaagcc gcgttgccag gttttacctt ccatttactg  4926
tagcaaatac tatcaaccag tcggacttct aagattcagt ttcagtttca gtacaatgcg  4986
gtgccactgt ttctcccatg tgctatggaa acgaatctat ctttgaactt aatgatgtat  5046
tcatagcaac tattactggt ttagattttt tccttttgtc acaggagtcc ctggaactag  5106
taactgaaaa tgttttcctg cgtttcttgt atacatgtga ttatgaaatt cgtgccattt  5166
aatgtcaatt tagctgtcac tagaagactg tctttggat atagtataaa tatttttatg  5226
```

-continued

```
taccagtgat gttctccata ccacggttac catgtttctc tggaggttgg gtctgtggtc   5286
tgatgtttct catgtgcagc ttcgatggga attcttctaa gtgggattta ttttcagat    5346 atttatgat atgagaatgt tattaatgaa gtaatttgaa agtgcattgt ataaaaatgg    5406
tcaccaagca atgcgtgaca gtaaaaggtc cgttttata aacctgcgca cattgttatt    5466
aaaatgtaag gttgaaaagg caatatttag aatatttcag atatatttt aaaaagtttt    5526 tccacagcta cttgagtttc atggtcttct agtatataac aacactcaag tctacccaga   5586
gtgtctcaac tatctgcttg tcaattctgc ttaatttat tttcatgcat ttaaactttt    5646
atatctttgt tagcatctct tccttatgat cctcatgtgt actattatgt aataaccaca   5706
tacatgtaat atccacatac atgtaatatc cacacatgta acattcacat acatgtagtc   5766
cagttattcc atcttgaccc tacctttcg aacccaaaag aaaattgttc ttgttattt     5826 tatttcttct gttatttgtg agatgaaccc gttcccttta aataatcttt gtttgtgcct   5886
tatgttcagt cattttaatt tgctgtcttc atgtcgaagc tgctggttc tcagccaaaa    5946 agcatcatct tagactctct aaatagccaa agcatcatga gtttggaatt taacatcagc   6006
tcccatgtca gagttgtgct cctcatgtga tcccacattc tactgcccag tgtagtgaat   6066
tcctttccaa gaactcttgc ctttgctttc caagttatt ttgagcatct tggttgcaga    6126
gatctcaaga atttacgtct tggattccac gttttcacta cgaagaaaca gaatgagaag   6186
aagaagaaaa attaggcagt gtagagctgg gcgtagtggt ccaggtcttt aagcccaggc   6246
tagcctgatt tagccaataa attctaggcc taaaaagaga gacctgtctc aaaactcaaa   6306
gcacacaaca gatgctaagt agatgggtct ccataattgg gaagccaatg agagaatgca   6366
tatttcttcc tatgttcttt aaaacttgaa gcagttacat ccgtctttca tcattacggg   6426
actcgtgcat tcagagcctt tgttgttct tttgccagaa tagatgaggc aacatttgcc    6486
tattcgaatg ctgtaacagg caagttgact ctagggttt ggtctgagac atttggtgaa    6546
caccttcaac actgattaaa atattactga atgcctactc ttatcctgat tatgaatctt   6606
ccagaataaa tagaatatta gctcatataa ttgttcagaa ttggagatgt atgcctacta   6666
ccctgtacct aaagggcaaa aatatcttca ctgtaatgtg tgtgcttctt caaggtgttt   6726
tgcttcttgt aaaagtgttt tcctttggct tgttactgcc ttttgtcaga taatcttgat   6786
gacgctgtat cataataaat attttctatt tatt                                6820
```

<210> SEQ ID NO 15
<211> LENGTH: 1199
<212> TYPE: PRT
<213> ORGANISM: Rattus norvegicus

<400> SEQUENCE: 15

```
Met Val Arg Leu Leu Leu Ile Phe Phe Pro Met Ile Phe Leu Glu Met
1               5                   10                  15

Ser Ile Leu Pro Arg Met Pro Asp Arg Lys Val Leu Leu Ala Gly Ala
            20                  25                  30

Ser Ser Gln Arg Ser Val Ala Arg Met Asp Gly Asp Val Ile Ile Gly
        35                  40                  45

Ala Leu Phe Ser Val His His Gln Pro Pro Ala Glu Lys Val Pro Glu
    50                  55                  60

Arg Lys Cys Gly Glu Ile Arg Glu Gln Tyr Gly Ile Gln Arg Val Glu
65                  70                  75                  80

Ala Met Phe His Thr Leu Asp Lys Ile Asn Ala Asp Pro Val Leu Leu
```

-continued

```
                    85                  90                  95
Pro Asn Ile Thr Leu Gly Ser Glu Ile Arg Asp Ser Cys Trp His Ser
                100                 105                 110
Ser Val Ala Leu Glu Gln Ser Ile Glu Phe Ile Arg Asp Ser Leu Ile
                115                 120                 125
Ser Ile Arg Asp Glu Lys Asp Gly Leu Asn Arg Cys Leu Pro Asp Gly
            130                 135                 140
Gln Thr Leu Pro Pro Gly Arg Thr Lys Lys Pro Ile Ala Gly Val Ile
145                 150                 155                 160
Gly Pro Gly Ser Ser Val Ala Ile Gln Val Gln Asn Leu Leu Gln
                165                 170                 175
Leu Phe Asp Ile Pro Gln Ile Ala Tyr Ser Ala Thr Ser Ile Asp Leu
                180                 185                 190
Ser Asp Lys Thr Leu Tyr Lys Tyr Phe Leu Arg Val Val Pro Ser Asp
            195                 200                 205
Thr Leu Gln Ala Arg Ala Met Leu Asp Ile Val Lys Arg Tyr Asn Trp
            210                 215                 220
Thr Tyr Val Ser Ala Val His Thr Glu Gly Asn Tyr Gly Glu Ser Gly
225                 230                 235                 240
Met Asp Ala Phe Lys Glu Leu Ala Ala Gln Glu Gly Leu Cys Ile Ala
                245                 250                 255
His Ser Asp Lys Ile Tyr Ser Asn Ala Gly Glu Lys Ser Phe Asp Arg
            260                 265                 270
Leu Leu Arg Lys Leu Arg Glu Arg Leu Pro Lys Ala Arg Val Val Val
            275                 280                 285
Cys Phe Cys Glu Gly Met Thr Val Arg Gly Leu Leu Ser Ala Met Arg
        290                 295                 300
Arg Leu Gly Val Val Gly Glu Phe Ser Leu Ile Gly Ser Asp Gly Trp
305                 310                 315                 320
Ala Asp Arg Asp Glu Val Ile Glu Gly Tyr Glu Val Glu Ala Asn Gly
                325                 330                 335
Gly Ile Thr Ile Lys Leu Gln Ser Pro Glu Val Arg Ser Phe Asp Asp
            340                 345                 350
Tyr Phe Leu Lys Leu Arg Leu Asp Thr Asn Thr Arg Asn Pro Trp Phe
            355                 360                 365
Pro Glu Phe Trp Gln His Arg Phe Gln Cys Arg Leu Pro Gly His Leu
        370                 375                 380
Leu Glu Asn Pro Asn Phe Lys Lys Val Cys Thr Gly Asn Glu Ser Leu
385                 390                 395                 400
Glu Glu Asn Tyr Val Gln Asp Ser Lys Met Gly Phe Val Ile Asn Ala
                405                 410                 415
Ile Tyr Ala Met Ala His Gly Leu Gln Asn Met His His Ala Leu Cys
            420                 425                 430
Pro Gly His Val Gly Leu Cys Asp Ala Met Lys Pro Ile Asp Gly Arg
            435                 440                 445
Lys Leu Leu Asp Phe Leu Ile Lys Ser Ser Phe Val Gly Val Ser Gly
450                 455                 460
Glu Glu Val Trp Phe Asp Glu Lys Gly Asp Ala Pro Gly Arg Tyr Asp
465                 470                 475                 480
Ile Met Asn Leu Gln Tyr Thr Glu Ala Asn Arg Tyr Asp Tyr Val His
                485                 490                 495
Val Gly Thr Trp His Glu Gly Val Leu Asn Ile Asp Asp Tyr Lys Ile
            500                 505                 510
```

-continued

```
Gln Met Asn Lys Ser Gly Met Val Arg Ser Val Cys Ser Glu Pro Cys
            515                 520                 525
Leu Lys Gly Gln Ile Lys Val Ile Arg Lys Gly Glu Val Ser Cys Cys
        530                 535                 540
Trp Ile Cys Thr Ala Cys Lys Glu Asn Glu Phe Val Gln Asp Glu Phe
545                 550                 555                 560
Thr Cys Arg Ala Cys Asp Leu Gly Trp Trp Pro Asn Ala Glu Leu Thr
                565                 570                 575
Gly Cys Glu Pro Ile Pro Val Arg Tyr Leu Glu Trp Ser Asp Ile Glu
            580                 585                 590
Ser Ile Ile Ala Ile Ala Phe Ser Cys Leu Gly Ile Leu Val Thr Leu
        595                 600                 605
Phe Val Thr Leu Ile Phe Val Leu Tyr Arg Asp Thr Pro Val Val Lys
    610                 615                 620
Ser Ser Ser Arg Glu Leu Cys Tyr Ile Ile Leu Ala Gly Ile Phe Leu
625                 630                 635                 640
Gly Tyr Val Cys Pro Phe Thr Leu Ile Ala Lys Pro Thr Thr Thr Ser
                645                 650                 655
Cys Tyr Leu Gln Arg Leu Leu Val Gly Leu Ser Ser Ala Met Cys Tyr
            660                 665                 670
Ser Ala Leu Val Thr Lys Thr Asn Arg Ile Ala Arg Ile Leu Ala Gly
        675                 680                 685
Ser Lys Lys Lys Ile Cys Thr Arg Lys Pro Arg Phe Met Ser Ala Trp
690                 695                 700
Ala Gln Val Ile Ile Ala Ser Ile Leu Ile Ser Val Gln Leu Thr Leu
705                 710                 715                 720
Val Val Thr Leu Ile Ile Met Glu Pro Pro Met Pro Ile Leu Ser Tyr
                725                 730                 735
Pro Ser Ile Lys Glu Val Tyr Leu Ile Cys Asn Thr Ser Asn Leu Gly
            740                 745                 750
Val Val Ala Pro Val Gly Tyr Asn Gly Leu Leu Ile Met Ser Cys Thr
        755                 760                 765
Tyr Tyr Ala Phe Lys Thr Arg Asn Val Pro Ala Asn Phe Asn Glu Ala
    770                 775                 780
Lys Tyr Ile Ala Phe Thr Met Tyr Thr Thr Cys Ile Ile Trp Leu Ala
785                 790                 795                 800
Phe Val Pro Ile Tyr Phe Gly Ser Asn Tyr Lys Ile Ile Thr Thr Cys
                805                 810                 815
Phe Ala Val Ser Leu Ser Val Thr Val Ala Leu Gly Cys Met Phe Thr
            820                 825                 830
Pro Lys Met Tyr Ile Ile Ala Lys Pro Glu Arg Asn Val Arg Ser
        835                 840                 845
Ala Phe Thr Thr Ser Asp Val Val Arg Met His Val Gly Asp Gly Lys
    850                 855                 860
Leu Pro Cys Arg Ser Asn Thr Phe Leu Asn Ile Phe Arg Arg Lys Lys
865                 870                 875                 880
Pro Gly Ala Gly Asn Ala Asn Ser Asn Gly Lys Ser Val Ser Trp Ser
                885                 890                 895
Glu Pro Gly Gly Arg Gln Ala Pro Lys Gly Gln His Val Trp Gln Arg
            900                 905                 910
Leu Ser Val His Val Lys Thr Asn Glu Thr Ala Cys Asn Gln Thr Ala
        915                 920                 925
```

-continued

```
Val Ile Lys Pro Leu Thr Lys Ser Tyr Gln Gly Ser Gly Lys Ser Leu
    930                 935                 940
Thr Phe Ser Asp Ala Ser Thr Lys Thr Leu Tyr Asn Val Glu Glu Glu
945                 950                 955                 960
Asp Asn Thr Pro Ser Ala His Phe Ser Pro Ser Ser Pro Ser Met
                965                 970                 975
Val Val His Arg Arg Gly Pro Pro Val Ala Thr Thr Pro Leu Pro
            980                 985                 990
Pro His Leu Thr Ala Glu Glu Thr  Pro Leu Phe Leu Ala  Asp Ser Val
            995                 1000                1005
Ile Pro  Lys Gly Leu Pro Pro  Pro Leu Pro Gln Gln  Gln Pro Gln
    1010                1015                1020
Gln Pro  Pro Pro Gln Gln Pro  Pro Gln Gln Pro Lys  Ser Leu Met
    1025                1030                1035
Asp Gln  Leu Gln Gly Val Val  Thr Asn Phe Gly Ser  Gly Ile Pro
    1040                1045                1050
Asp Phe  His Ala Val Leu Ala  Gly Pro Gly Thr Pro  Gly Asn Ser
    1055                1060                1065
Leu Arg  Ser Leu Tyr Pro Pro  Pro Pro Pro Pro Gln  His Leu Gln
    1070                1075                1080
Met Leu  Pro Leu His Leu Ser  Thr Phe Gln Glu Glu  Ser Ile Ser
    1085                1090                1095
Pro Pro  Gly Glu Asp Ile Asp  Asp Ser Glu Arg  Phe Lys Leu
    1100                1105                1110
Leu Gln  Glu Phe Val Tyr Glu  Arg Glu Gly Asn Thr  Glu Glu Asp
    1115                1120                1125
Glu Leu  Glu Glu Glu Glu Asp  Leu Pro Thr Ala Ser  Lys Leu Thr
    1130                1135                1140
Pro Glu  Asp Ser Pro Ala Leu  Thr Pro Pro Ser Pro  Phe Arg Asp
    1145                1150                1155
Ser Val  Ala Ser Gly Ser Ser  Val Pro Ser Ser Pro  Val Ser Glu
    1160                1165                1170
Ser Val  Leu Cys Thr Pro Pro  Asn Val Thr Tyr Ala  Ser Val Ile
    1175                1180                1185
Leu Arg  Asp Tyr Lys Gln Ser  Ser Ser Thr Leu
    1190                1195
```

<210> SEQ ID NO 16
<211> LENGTH: 432
<212> TYPE: DNA
<213> ORGANISM: Artificial
<220> FEATURE:
<223> OTHER INFORMATION: probe

<400> SEQUENCE: 16

```
acgacctctg atgttgtccg catgcacgtc ggtgatggca aactgccgtg ccgctccaac      60
accttcctca acatttccg gagaaagaag cccggggcag ggaatgccaa ttctaacggc     120
aagtctgtgt catggtctga accaggtgga agacaggcgc ccaagggaca gcacgtgtgg     180
cagcgcctct ctgtgcacgt gaagaccaac gagacggcct gtaaccaaac agccgtaatc     240
aaacccctca ctaaaagtta ccaaggctct ggcaagagcc tgaccttttc agatgccagc     300
accaaggagt gtcaacccct tccagaaatgt gtagaaagca gggtgaggga tggggatgga     360
ggaccacggt ctgcagggaa gaaaaaaaaa atgctgcggc tgccttaaag aaggagaggg     420
acgatgccaa ct                                                          432
```

```
<210> SEQ ID NO 17
<211> LENGTH: 646
<212> TYPE: DNA
<213> ORGANISM: Artificial
<220> FEATURE:
<223> OTHER INFORMATION: probe

<400> SEQUENCE: 17
cactagtggt gaccttgatc atcatggagc ctcccatgcc cattttgtcc tacccgagta      60
tcaaggaagt ctaccttatc tgcaatacca gcaacctggg tgtagtggcc cctgtgggtt     120
acaatggact cctcatcatg agctgtacct actatgcctt caagacccgc aacgtgccgg     180
ccaacttcaa tgaggctaaa tacatcgcct tcaccatgta cactacctgc atcatctggc     240
tggctttcgt tcccatttac tttgggagca actacaagat catcactacc tgcttcgcgg     300
tgagcctcag tgtgacggtg gccctggggt gcatgtttac tccgaagatg tacatcatca     360
ttgccaaacc tgagaggaac gtccgcagtg ccttcacgac ctctgatgtt gtccgcatgc     420
acgtcggtga tggcaaactg ccgtgccgct ccaacacctt cctcaacatt ttccggagaa     480
agaagcccgg ggcagggaat gccaattcta acggcaagtc tgtgtcatgg tctgaaccag     540
gtggaagaca ggcgcccaag ggacagcacg tgtggcagcg cctctctgtg cacgtgaaga     600
ccaacgagac ggcctgtaac caaacagccg taatcaaacc cctcac                    646

<210> SEQ ID NO 18
<211> LENGTH: 33
<212> TYPE: PRT
<213> ORGANISM: Rattus norvegicus

<400> SEQUENCE: 18

Glu Cys Gln Pro Phe Gln Lys Cys Val Glu Ser Arg Val Arg Asp Gly
1               5                   10                  15

Asp Gly Gly Pro Arg Ser Ala Gly Lys Lys Lys Met Leu Arg Leu
            20                  25                  30

Pro

<210> SEQ ID NO 19
<211> LENGTH: 3038
<212> TYPE: DNA
<213> ORGANISM: Rattus norvegicus
<220> FEATURE:
<221> NAME/KEY: CDS
<222> LOCATION: (442)..(2814)
<223> OTHER INFORMATION:
<220> FEATURE:
<221> NAME/KEY: misc_feature
<223> OTHER INFORMATION: mGluR1 beta-a, taste cDNA

<400> SEQUENCE: 19
gggactctct cctgtcttgt gaggctgaag cataacaggg aattgcagtg gcttaaagta      60
gactttggct tctctggatt gctttgttta tagatatctc tgaactcatt tgtgagacac     120
tgtcttcttc ttctctcttc accccaaccc ctgcattgtt ttagtgatgg atgggcagac     180
agagatgaag tcatcgaagg ctatgaggtg gaagccaacg gagggatcac aataaagctt     240
cagtctccag aggtcaggtc atttgatgac tacttcctga agctgaggct ggacaccaac     300
acaaggaatc cttggttccc tgagttctgg caacatcgct tccagtgtcg cctacctgga     360
cacctcttgg aaaaccccaa ctttaagaaa gtgtgcacag gaaatgaaag cttggaagaa     420
aactatgtcc aggacagcaa a atg gga ttt gtc atc aat gcc atc tat gcc      471
```

```
                              Met Gly Phe Val Ile Asn Ala Ile Tyr Ala
                                1               5                  10 atg gca cat ggg ctg cag aac atg cac cat gct ctg tgt ccc ggc cat              519
Met Ala His Gly Leu Gln Asn Met His His Ala Leu Cys Pro Gly His
             15                  20                  25 gtg ggc ctg tgt gat gct atg aaa ccc att gat ggc agg aag ctc ctg              567
Val Gly Leu Cys Asp Ala Met Lys Pro Ile Asp Gly Arg Lys Leu Leu
         30                  35                  40 gat ttc ctc atc aaa tcc tct ttt gtc gga gtg tct gga gag gag gtg              615
Asp Phe Leu Ile Lys Ser Ser Phe Val Gly Val Ser Gly Glu Glu Val
             45                  50                  55 tgg ttc gat gag aag ggg gat gct ccc gga agg tat gac att atg aat              663
Trp Phe Asp Glu Lys Gly Asp Ala Pro Gly Arg Tyr Asp Ile Met Asn
     60                  65                  70 ctg cag tac aca gaa gct aat cgc tat gac tat gtc cac gtg ggg acc              711
Leu Gln Tyr Thr Glu Ala Asn Arg Tyr Asp Tyr Val His Val Gly Thr
75                  80                  85                  90 tgg cat gaa gga gtg ctg aat att gat gat tac aaa atc cag atg aac              759
Trp His Glu Gly Val Leu Asn Ile Asp Asp Tyr Lys Ile Gln Met Asn
                 95                 100                 105 aaa agc gga atg gta cga tct gtg tgc agt gag cct tgc tta aag ggt              807
Lys Ser Gly Met Val Arg Ser Val Cys Ser Glu Pro Cys Leu Lys Gly
             110                 115                 120 cag att aag gtc ata cgg aaa gga gaa gtg agc tgc tgc tgg atc tgc              855
Gln Ile Lys Val Ile Arg Lys Gly Glu Val Ser Cys Cys Trp Ile Cys
         125                 130                 135 acg gcc tgc aaa gag aat gag ttt gtg cag gac gag ttc acc tgc aga              903
Thr Ala Cys Lys Glu Asn Glu Phe Val Gln Asp Glu Phe Thr Cys Arg
     140                 145                 150 gcc tgt gac ctg ggg tgg tgg ccc aac gca gag ctc aca ggc tgt gag              951
Ala Cys Asp Leu Gly Trp Trp Pro Asn Ala Glu Leu Thr Gly Cys Glu
155                 160                 165                 170 ccc att cct gtc cgt tat ctt gag tgg agt gac ata gaa tct atc ata              999
Pro Ile Pro Val Arg Tyr Leu Glu Trp Ser Asp Ile Glu Ser Ile Ile
                 175                 180                 185 gcc atc gcc ttt tct tgc ctg ggc atc ctc gtg acg ctg ttt gtc acc             1047
Ala Ile Ala Phe Ser Cys Leu Gly Ile Leu Val Thr Leu Phe Val Thr
             190                 195                 200 ctc atc ttc gtt ctg tac cgg gac aca ccc gtg gtc aaa tcc tcc agt             1095
Leu Ile Phe Val Leu Tyr Arg Asp Thr Pro Val Val Lys Ser Ser Ser
         205                 210                 215 agg gag ctc tgc tat atc att ctg gct ggt att ttc ctc ggc tat gtg             1143
Arg Glu Leu Cys Tyr Ile Ile Leu Ala Gly Ile Phe Leu Gly Tyr Val
     220                 225                 230 tgc cct ttc acc ctc atc gcc aaa cct act acc aca tcc tgc tac ctc             1191
Cys Pro Phe Thr Leu Ile Ala Lys Pro Thr Thr Thr Ser Cys Tyr Leu
235                 240                 245                 250 cag cgc ctc cta gtt ggc ctc tct tct gcc atg tgc tac tct gct tta             1239
Gln Arg Leu Leu Val Gly Leu Ser Ser Ala Met Cys Tyr Ser Ala Leu
                 255                 260                 265 gtg acc aaa acc aat cgt att gca cgc atc ctg gct ggc agc aag aag             1287
Val Thr Lys Thr Asn Arg Ile Ala Arg Ile Leu Ala Gly Ser Lys Lys
             270                 275                 280 aag atc tgc acc cgg aag ccc aga ttc atg agc gct tgg gcc caa gtg             1335
Lys Ile Cys Thr Arg Lys Pro Arg Phe Met Ser Ala Trp Ala Gln Val
         285                 290                 295 atc ata gcc tcc att ctg att agt gta cag cta aca cta gtg gtg acc             1383
Ile Ile Ala Ser Ile Leu Ile Ser Val Gln Leu Thr Leu Val Val Thr
     300                 305                 310
```

```
ttg atc atc atg gag cct ccc atg ccc att ttg tcc tac ccg agt atc   1431
Leu Ile Ile Met Glu Pro Pro Met Pro Ile Leu Ser Tyr Pro Ser Ile
315                 320                 325                 330 aag gaa gtc tac ctt atc tgc aat acc agc aac ctg ggt gta gtg gcc   1479
Lys Glu Val Tyr Leu Ile Cys Asn Thr Ser Asn Leu Gly Val Val Ala
            335                 340                 345 cct gtg ggt tac aat gga ctc ctc atc atg agc tgt acc tac tat gcc   1527
Pro Val Gly Tyr Asn Gly Leu Leu Ile Met Ser Cys Thr Tyr Tyr Ala
        350                 355                 360 ttc aag acc cgc aac gtg ccg gcc aac ttc aat gag gct aaa tac atc   1575
Phe Lys Thr Arg Asn Val Pro Ala Asn Phe Asn Glu Ala Lys Tyr Ile
    365                 370                 375 gcc ttc acc atg tac act acc tgc atc atc tgg ctg gct ttc gtt ccc   1623
Ala Phe Thr Met Tyr Thr Thr Cys Ile Ile Trp Leu Ala Phe Val Pro
380                 385                 390 att tac ttt ggg agc aac tac aag atc atc act acc tgc ttc gcg gtg   1671
Ile Tyr Phe Gly Ser Asn Tyr Lys Ile Ile Thr Thr Cys Phe Ala Val
395                 400                 405                 410 agc ctc agt gtg acg gtg gcc ctg ggg tgc atg ttt act ccg aag atg   1719
Ser Leu Ser Val Thr Val Ala Leu Gly Cys Met Phe Thr Pro Lys Met
            415                 420                 425 tac atc atc att gcc aaa cct gag agg aac gtc cgc agt gcc ttc acg   1767
Tyr Ile Ile Ile Ala Lys Pro Glu Arg Asn Val Arg Ser Ala Phe Thr
        430                 435                 440 acc tct gat gtt gtc cgc atg cac gtc ggt gat ggc aaa ctg ccg tgc   1815
Thr Ser Asp Val Val Arg Met His Val Gly Asp Gly Lys Leu Pro Cys
    445                 450                 455 cgc tcc aac acc ttc ctc aac att ttc cgg aga aag aag ccc ggg gca   1863
Arg Ser Asn Thr Phe Leu Asn Ile Phe Arg Arg Lys Lys Pro Gly Ala
460                 465                 470 ggg aat gcc aat tct aac ggc aag tct gtg tca tgg tct gaa cca ggt   1911
Gly Asn Ala Asn Ser Asn Gly Lys Ser Val Ser Trp Ser Glu Pro Gly
475                 480                 485                 490 gga aga cag gcg ccc aag gga cag cac gtg tgg cag cgc ctc tct gtg   1959
Gly Arg Gln Ala Pro Lys Gly Gln His Val Trp Gln Arg Leu Ser Val
            495                 500                 505 cac gtg aag acc aac gag acg gcc tgt aac caa aca gcc gta atc aaa   2007
His Val Lys Thr Asn Glu Thr Ala Cys Asn Gln Thr Ala Val Ile Lys
        510                 515                 520 ccc ctc act aaa agt tac caa ggc tct ggc aag agc ctg acc ttt tca   2055
Pro Leu Thr Lys Ser Tyr Gln Gly Ser Gly Lys Ser Leu Thr Phe Ser
    525                 530                 535 gat gcc agc acc aag acc ctt tac aat gtg gaa gaa gag gac aat acc   2103
Asp Ala Ser Thr Lys Thr Leu Tyr Asn Val Glu Glu Glu Asp Asn Thr
540                 545                 550 cct tct gct cac ttc agc cct ccc agc agc cct tct atg gtg gtg cac   2151
Pro Ser Ala His Phe Ser Pro Pro Ser Ser Pro Ser Met Val Val His
555                 560                 565                 570 cga cgc ggg cca ccc gtg gcc acc aca cca cct ctg cca ccc cat ctg   2199
Arg Arg Gly Pro Pro Val Ala Thr Thr Pro Pro Leu Pro Pro His Leu
            575                 580                 585 acc gca gaa gag acc ccc ctg ttc ctg gct gat tcc gtc atc ccc aag   2247
Thr Ala Glu Glu Thr Pro Leu Phe Leu Ala Asp Ser Val Ile Pro Lys
        590                 595                 600 ggc ttg cct cct cct ctc ccg cag cag cag cca cag cag ccg ccc cct   2295
Gly Leu Pro Pro Pro Leu Pro Gln Gln Gln Pro Gln Gln Pro Pro Pro
    605                 610                 615 cag cag ccc ccg cag cag ccc aag tcc ctg atg gac cag ctg caa ggc   2343
Gln Gln Pro Pro Gln Gln Pro Lys Ser Leu Met Asp Gln Leu Gln Gly
620                 625                 630
```

-continued

```
gta gtc acc aac ttc ggt tcg ggg att cca gat ttc cat gcg gtg ctg        2391
Val Val Thr Asn Phe Gly Ser Gly Ile Pro Asp Phe His Ala Val Leu
635                 640                 645                 650 gca ggc ccg ggg aca cca gga aac agc ctg cgc tct ctg tac ccg ccc        2439
Ala Gly Pro Gly Thr Pro Gly Asn Ser Leu Arg Ser Leu Tyr Pro Pro
            655                 660                 665 ccg cct ccg ccg caa cac ctg cag atg ctg ccc ctg cac ctg agc acc        2487
Pro Pro Pro Pro Gln His Leu Gln Met Leu Pro Leu His Leu Ser Thr
        670                 675                 680 ttc cag gag gag tcc atc tcc cct cct ggg gag gac atc gat gat gac        2535
Phe Gln Glu Glu Ser Ile Ser Pro Pro Gly Glu Asp Ile Asp Asp Asp
    685                 690                 695 agt gag aga ttc aag ctc ctg cag gag ttc gtg tac gag cgc gaa ggg        2583
Ser Glu Arg Phe Lys Leu Leu Gln Glu Phe Val Tyr Glu Arg Glu Gly
700                 705                 710 aac acc gaa gaa gat gaa ttg gaa gag gag gag gac ctg ccc aca gcc        2631
Asn Thr Glu Glu Asp Glu Leu Glu Glu Glu Asp Leu Pro Thr Ala
715                 720                 725                 730 agc aag ctg acc cct gag gat tct cct gcc ctg acg cct cct tct cct        2679
Ser Lys Leu Thr Pro Glu Asp Ser Pro Ala Leu Thr Pro Pro Ser Pro
            735                 740                 745 ttc cga gat tcc gtg gcc tct ggc agc tca gtg ccc agt tcc ccc gta        2727
Phe Arg Asp Ser Val Ala Ser Gly Ser Ser Val Pro Ser Ser Pro Val
        750                 755                 760 tct gag tcg gtc ctc tgc acc cct cca aat gta acc tac gcc tct gtc        2775
Ser Glu Ser Val Leu Cys Thr Pro Pro Asn Val Thr Tyr Ala Ser Val
    765                 770                 775 att ctg agg gac tac aag caa agc tct tcc acc ctg tag tgtgtgtgtg        2824
Ile Leu Arg Asp Tyr Lys Gln Ser Ser Ser Thr Leu
780                 785                 790 tgtgtggggg cgggggggagt gcgcatggag aagccagaga tgccaaggag tgtcaaccct    2884
tccagaaatg tgtagaaagc agggtgaggg atggggatgg aggaccacgg tctgcaggga    2944
agaaaaaaaa aatgctgcgg ctgccttaaa gaaggagagg gacgatgcca actgaacagt    3004
ggtcctggcc aggattgtga ctcttgaatt attc                                 3038
```

<210> SEQ ID NO 20
<211> LENGTH: 790
<212> TYPE: PRT
<213> ORGANISM: Rattus norvegicus

<400> SEQUENCE: 20

```
Met Gly Phe Val Ile Asn Ala Ile Tyr Ala Met Ala His Gly Leu Gln
1               5                   10                  15

Asn Met His His Ala Leu Cys Pro Gly His Val Gly Leu Cys Asp Ala
            20                  25                  30

Met Lys Pro Ile Asp Gly Arg Lys Leu Leu Asp Phe Leu Ile Lys Ser
        35                  40                  45

Ser Phe Val Gly Val Ser Gly Glu Glu Val Trp Phe Asp Glu Lys Gly
    50                  55                  60

Asp Ala Pro Gly Arg Tyr Asp Ile Met Asn Leu Gln Tyr Thr Glu Ala
65                  70                  75                  80

Asn Arg Tyr Asp Tyr Val His Val Gly Thr Trp His Glu Gly Val Leu
                85                  90                  95

Asn Ile Asp Asp Tyr Lys Ile Gln Met Asn Lys Ser Gly Met Val Arg
            100                 105                 110

Ser Val Cys Ser Glu Pro Cys Leu Lys Gly Gln Ile Lys Val Ile Arg
```

-continued

```
            115                 120                 125
Lys Gly Glu Val Ser Cys Cys Trp Ile Cys Thr Ala Cys Lys Glu Asn
    130                 135                 140
Glu Phe Val Gln Asp Glu Phe Thr Cys Arg Ala Cys Asp Leu Gly Trp
145                 150                 155                 160
Trp Pro Asn Ala Glu Leu Thr Gly Cys Glu Pro Ile Pro Val Arg Tyr
                165                 170                 175
Leu Glu Trp Ser Asp Ile Glu Ser Ile Ile Ala Ile Ala Phe Ser Cys
                180                 185                 190
Leu Gly Ile Leu Val Thr Leu Phe Val Thr Leu Ile Phe Val Leu Tyr
                195                 200                 205
Arg Asp Thr Pro Val Val Lys Ser Ser Arg Glu Leu Cys Tyr Ile
    210                 215                 220
Ile Leu Ala Gly Ile Phe Leu Gly Tyr Val Cys Pro Phe Thr Leu Ile
225                 230                 235                 240
Ala Lys Pro Thr Thr Thr Ser Cys Tyr Leu Gln Arg Leu Leu Val Gly
                245                 250                 255
Leu Ser Ser Ala Met Cys Tyr Ser Ala Leu Val Thr Lys Thr Asn Arg
                260                 265                 270
Ile Ala Arg Ile Leu Ala Gly Ser Lys Lys Ile Cys Thr Arg Lys
    275                 280                 285
Pro Arg Phe Met Ser Ala Trp Ala Gln Val Ile Ile Ala Ser Ile Leu
    290                 295                 300
Ile Ser Val Gln Leu Thr Leu Val Val Thr Leu Ile Ile Met Glu Pro
305                 310                 315                 320
Pro Met Pro Ile Leu Ser Tyr Pro Ser Ile Lys Glu Val Tyr Leu Ile
                325                 330                 335
Cys Asn Thr Ser Asn Leu Gly Val Val Ala Pro Val Gly Tyr Asn Gly
                340                 345                 350
Leu Leu Ile Met Ser Cys Thr Tyr Tyr Ala Phe Lys Thr Arg Asn Val
                355                 360                 365
Pro Ala Asn Phe Asn Glu Ala Lys Tyr Ile Ala Phe Thr Met Tyr Thr
    370                 375                 380
Thr Cys Ile Ile Trp Leu Ala Phe Val Pro Ile Tyr Phe Gly Ser Asn
385                 390                 395                 400
Tyr Lys Ile Ile Thr Thr Cys Phe Ala Val Ser Leu Ser Val Thr Val
                405                 410                 415
Ala Leu Gly Cys Met Phe Thr Pro Lys Met Tyr Ile Ile Ile Ala Lys
                420                 425                 430
Pro Glu Arg Asn Val Arg Ser Ala Phe Thr Thr Ser Asp Val Val Arg
                435                 440                 445
Met His Val Gly Asp Gly Lys Leu Pro Cys Arg Ser Asn Thr Phe Leu
    450                 455                 460
Asn Ile Phe Arg Arg Lys Lys Pro Gly Ala Gly Asn Ala Asn Ser Asn
465                 470                 475                 480
Gly Lys Ser Val Ser Trp Ser Glu Pro Gly Gly Arg Gln Ala Pro Lys
                485                 490                 495
Gly Gln His Val Trp Gln Arg Leu Ser Val His Val Lys Thr Asn Glu
                500                 505                 510
Thr Ala Cys Asn Gln Thr Ala Val Ile Lys Pro Leu Thr Lys Ser Tyr
    515                 520                 525
Gln Gly Ser Gly Lys Ser Leu Thr Phe Ser Asp Ala Ser Thr Lys Thr
    530                 535                 540
```

-continued

```
Leu Tyr Asn Val Glu Glu Asp Asn Thr Pro Ser Ala His Phe Ser
545                 550                 555                 560

Pro Pro Ser Ser Pro Ser Met Val Val His Arg Arg Gly Pro Pro Val
                565                 570                 575

Ala Thr Thr Pro Pro Leu Pro Pro His Leu Thr Ala Glu Glu Thr Pro
            580                 585                 590

Leu Phe Leu Ala Asp Ser Val Ile Pro Lys Gly Leu Pro Pro Pro Leu
        595                 600                 605

Pro Gln Gln Gln Pro Gln Gln Pro Pro Gln Gln Pro Pro Gln Gln
    610                 615                 620

Pro Lys Ser Leu Met Asp Gln Leu Gln Gly Val Val Thr Asn Phe Gly
625                 630                 635                 640

Ser Gly Ile Pro Asp Phe His Ala Val Leu Ala Gly Pro Gly Thr Pro
                645                 650                 655

Gly Asn Ser Leu Arg Ser Leu Tyr Pro Pro Pro Pro Gln His
            660                 665                 670

Leu Gln Met Leu Pro Leu His Leu Ser Thr Phe Gln Glu Glu Ser Ile
            675                 680                 685

Ser Pro Pro Gly Glu Asp Ile Asp Asp Asp Ser Glu Arg Phe Lys Leu
690                 695                 700

Leu Gln Glu Phe Val Tyr Glu Arg Glu Gly Asn Thr Glu Glu Asp Glu
705                 710                 715                 720

Leu Glu Glu Glu Glu Asp Leu Pro Thr Ala Ser Lys Leu Thr Pro Glu
                725                 730                 735

Asp Ser Pro Ala Leu Thr Pro Pro Ser Pro Phe Arg Asp Ser Val Ala
            740                 745                 750

Ser Gly Ser Ser Val Pro Ser Ser Pro Val Ser Glu Ser Val Leu Cys
        755                 760                 765

Thr Pro Pro Asn Val Thr Tyr Ala Ser Val Ile Leu Arg Asp Tyr Lys
    770                 775                 780

Gln Ser Ser Ser Thr Leu
785                 790

<210> SEQ ID NO 21
<211> LENGTH: 23
<212> TYPE: DNA
<213> ORGANISM: Artificial
<220> FEATURE:
<223> OTHER INFORMATION: primer, mGluR1-50F

<400> SEQUENCE: 21
gagaccaata gctgtgtcta ccc                                          23

<210> SEQ ID NO 22
<211> LENGTH: 23
<212> TYPE: DNA
<213> ORGANISM: Artificial
<220> FEATURE:
<223> OTHER INFORMATION: primer, mGluR1-790-1F

<400> SEQUENCE: 22
gggactctct cctgtcttgt gag                                          23

<210> SEQ ID NO 23
<211> LENGTH: 23
<212> TYPE: DNA
<213> ORGANISM: Artificial
<220> FEATURE:
```

-continued

<223> OTHER INFORMATION: primer, mGluR1-790-2F

<400> SEQUENCE: 23
agcataacag ggaattgcag tgg 23